United States Patent [19]

Kuwata et al.

[11] Patent Number: 5,262,881
[45] Date of Patent: Nov. 16, 1993

[54] DRIVING METHOD OF DRIVING A LIQUID CRYSTAL DISPLAY ELEMENT

[75] Inventors: Takeshi Kuwata; Temkar Ruckmongathan; Yutaka Nakagawa; Hidemasa Koh; Hiroshi Hasebe; Takashi Yamashita; Hideyuki Nagano; Takanori Ohnishi, all of Yokohama, Japan

[73] Assignee: Asahi Glass Company Ltd., Tokyo, Japan

[21] Appl. No.: 910,513

[22] Filed: Jul. 8, 1992

[30] Foreign Application Priority Data

| Jul. 8, 1991 | [JP] | Japan | 3-193502 |
| Aug. 16, 1991 | [JP] | Japan | 3-229606 |
| Apr. 22, 1992 | [JP] | Japan | 4-129714 |
| May 15, 1992 | [JP] | Japan | 4-148844 |
| May 15, 1992 | [JP] | Japan | 4-148845 |

[51] Int. Cl.$^5$ .................. G02F 1/133; G09G 3/36
[52] U.S. Cl. .......................... 359/55; 345/93; 345/210
[58] Field of Search .............. 359/55, 102; 340/724, 340/755, 784, 793, 805; 358/53

[56] References Cited

U.S. PATENT DOCUMENTS

| 4,710,766 | 12/1987 | Dubois et al. | 340/784 |
| 5,119,085 | 6/1992 | Yamazaki | 359/55 |

Primary Examiner—William L. Sikes
Assistant Examiner—Huy K. Mai
Attorney, Agent, or Firm—Oblon, Spivak, McClelland, Maier & Neustadt

[57] ABSTRACT

A driving method of a matrix type liquid crystal display element comprising at least $J \times L$ number (J subgroup) of row electrodes and a plurality of column electrodes. When information of the j-th row electrode subgroup in a specified column is expressed by a column vector $D_j$ having an L number of elements, the following conditions are satisfied: (1) and j-th row electrode subgroup is selected so that the elements of a selection voltage vector which constitute a selection voltage matrix in which the product of a matrix and a transposed matrix of the same assumes a scalar multiple of the unit matrix is selected, and the selection voltage matrix comprising election voltage vectors arranged in a matrix are selected, and (2) when the j-th row electrode subgroup is selected, the voltage applied to the column electrodes to indicate a display information by means of the vector $D_j$ are determined as in the following items (a) and (b): (a) a vector $\beta$ is formed by the selection voltages applied to the j-th row electrode subgroup, and (b) a voltage $V_i (i = D, 1 \ldots L)$ given by the sum of exclusive OR of the elements corresponding to the vectors $\beta$ and $D_j$ is applied to the column electrodes.

14 Claims, 14 Drawing Sheets

R1 − C9(ON)

R2 − C9(OFF)

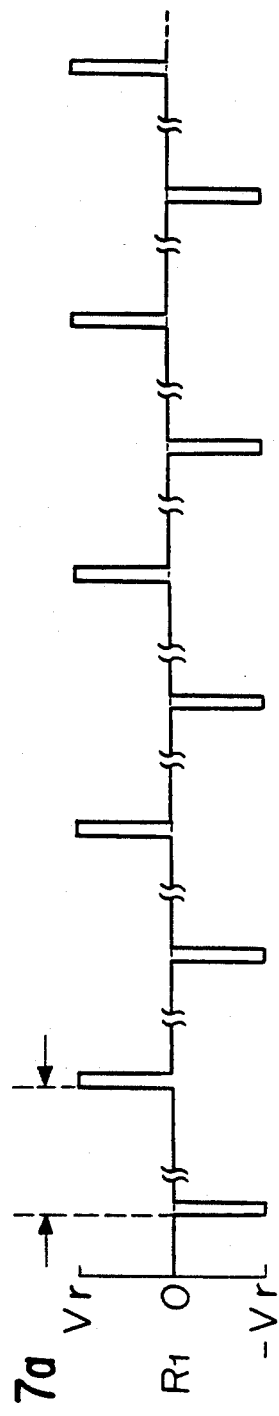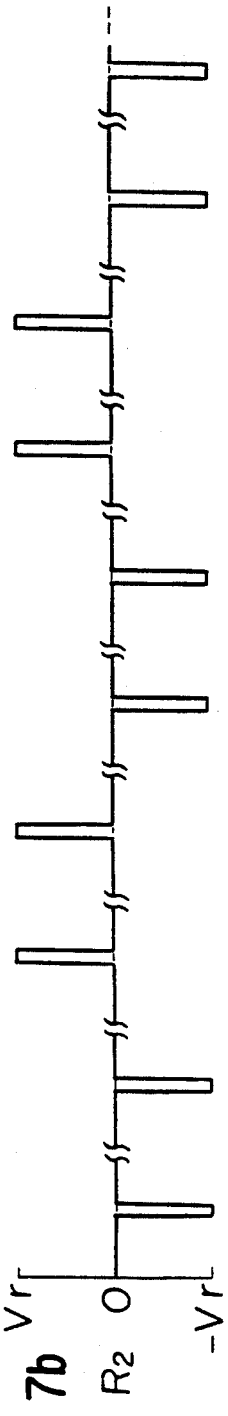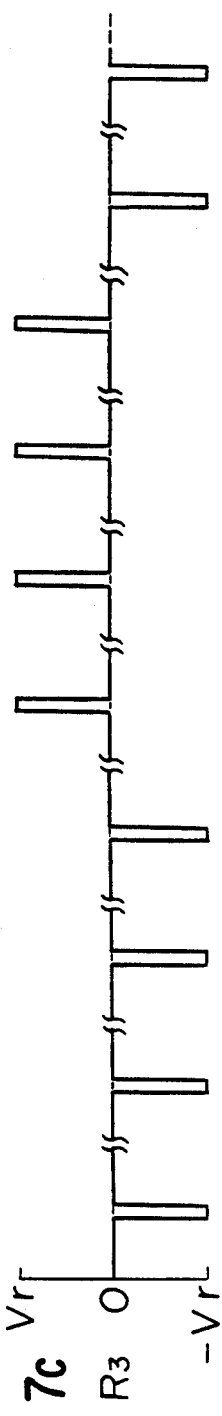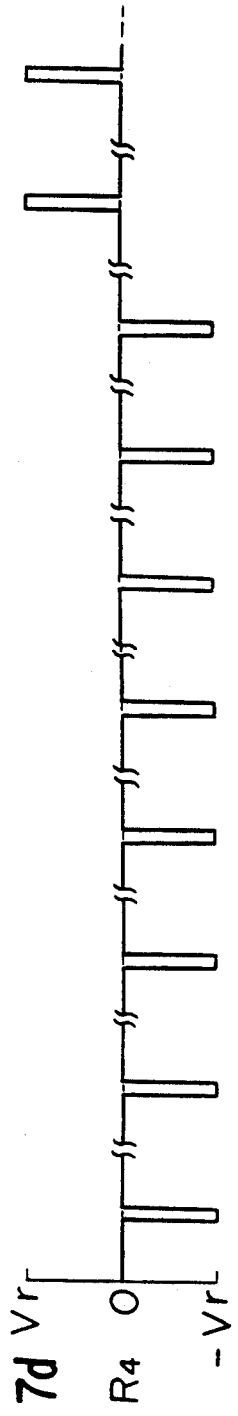
FIGURE 7a
FIGURE 7b
FIGURE 7c
FIGURE 7d

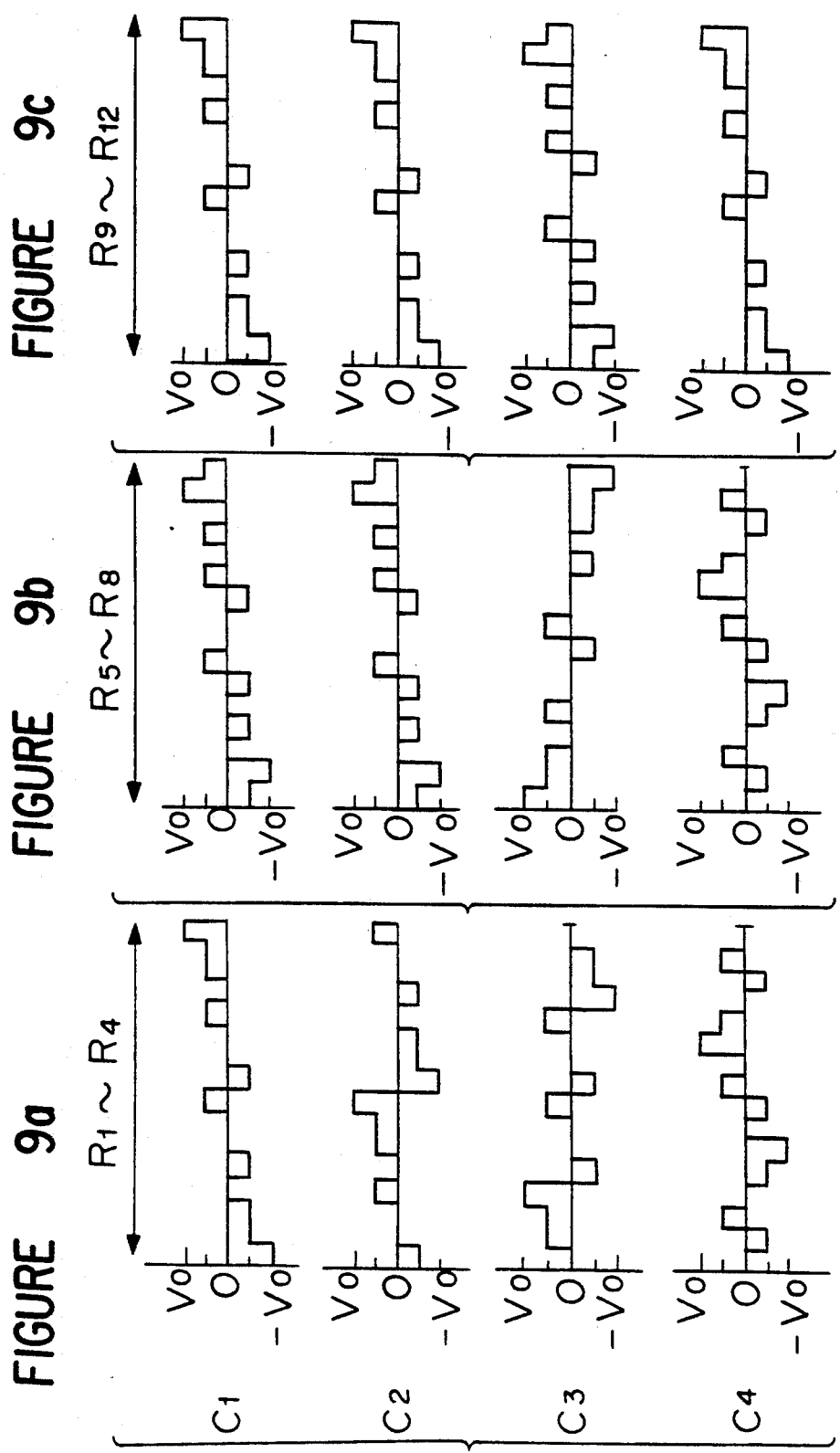

R1-C9 (ON)

R2-C9 (OFF)

DRIVING METHOD OF DRIVING A LIQUID CRYSTAL DISPLAY ELEMENT

The present invention relates to a method of driving a liquid crystal display element to display fast moving images.

In recent years, liquid crystal display elements have been noted as devices which are thin, light, compact and capable of displaying a large capacity of information, in place of CRTs. As driving methods to such liquid crystal display elements, they are mainly classified into two methods wherein each picture element of a twisted nematic type liquid crystal display element is driven by a thin-film transistor which is disposed in correspondence to each of the picture elements, and a twisted nematic type or a super-twisted nematic type liquid crystal display element is driven without using a thin-film transistor (a simple matrix type).

Although the liquid crystal display element with a thin film transistor can be driven at a relatively high speed, there is a problem that manufacturing steps for preparing the element are complicated and manufacturing cost is high. On the other hand, although manufacturing steps for the simple matrix type liquid crystal display element are relatively simple, there is a problem that it is difficult to switch a display picture at a high speed, whereby it is difficult to obtain a quick response in a display with a mouse at a terminal device when displaying video images.

The reason why it is difficult to drive the simple matrix type liquid crystal display element satisfactorily at a high speed is because the time required for orienting the liquid crystal molecules is large when a voltage is applied to the liquid crystal, which is inherent in the characteristics of the twisted nematic type or the super-twisted nematic type liquid crystal display element. Namely, in such liquid crystal display element having an average response time of about 250 msec, it is impossible to switch a display element or pixel at 20 Hz–30 Hz (which corresponds to a switching time of 33–50 msec) which is generally required in video display.

For high-speed driving, it is considered to use a liquid crystal element having a low response time to a voltage applied to liquid crystal. Such liquid crystal element is called a fast response type liquid crystal element. In order to obtain such fast response type liquid crystal element, there are such a method of using liquid crystal having a low viscosity and such a method that the thickness of the liquid crystal layer is reduced by using liquid crystal having a large refractive index anisotropy.

The response time of the super-twisted nematic type liquid crystal display element is generally in proportion to the viscosity $\eta$ of the liquid crystal used and is in proportion to the square of the thickness d of the liquid crystal layer used. On the other hand, in consideration of the demand that the product of the refractive index anisotropy $\Delta n$ of the super-twisted nematic type liquid crystal display element and the thickness d of the liquid crystal layer should be substantially constant, the response time of the liquid crystal display element is in proportion to the viscosity $\eta$ and is in inverse proportion to the square of the refractive index anisotropy $\Delta n$. Namely, it is preferable that the thickness d of the liquid crystal layer is small, and liquid crystal having a low viscosity and a large refractive index anisotropy is used for the liquid crystal element.

However, even though a fast response type liquid crystal element can be obtained in a manner as described above, use of such element has encountered an extremely large problem, which is described below. Generally, a method called optimized amplitude selective addressing method (e.g. "LIQUID CRYSTAL TV DISPLAYS" by E. Kaneko, 1987, published by KTK Scientific Publishers) has been used for driving a simple matrix type liquid crystal display element. In the waveform of a voltage applied to line electrodes in the optimized amplitude selective addressing method wherein the number of scanning lines (the number of row electrodes) is N and the frame period is $T_F$, there is a single selection pulse in the frame period T and a bias wave having a amplitude, which is 1/b as high as an ON voltage selection pulse, in a time other than the application of the selection pulse. Namely, a time of $T_F/N$ is assigned to in a selection time period and a time of $(N-1)T_F/N$ is assigned to a non-selection time period. In FIG. 5a, a symbol A shows a typical waveform of a voltage applied, wherein the abscissa represents time and the ordinate represents voltage. In many cases, two frames are used so as to form an a.c. voltage (d.c. free operation).

In the optimized amplitude selective addressing method, the response characteristic of liquid crystal molecules is effected by the r.m.s. value of the applied voltage to thereby be obtainable a predetermined contrast ratio of display. In FIG. 5b, a symbol C shows a curve of effective value to which the liquid crystal molecules are responsive to the applied voltage wherein the abscissa represents time and the ordinate represents the intensity of transmitting light in a case that polarization plates are arranged at both sides of the liquid crystal layer and an ON voltage is applied to the column electrodes at the time of selection of the line electrodes. Generally, a frame period of about 10 msec–several 10 msec is used, whereas the average response time of a normally used liquid crystal display element is about 250 msec. Accordingly, switching a single pixel of ON or OFF is completed by using several numbers of frames through ten and several numbers of frames.

When a fast response type liquid crystal display element is driven, a change in the direction of the axis of the liquid crystal molecules is apt to follow to the amplitude of voltage applied to the liquid crystal. Accordingly, the transmission of light through the cell as indicated by a wave B in FIG. 5b, the liquid crystal molecules are responsive to peak values, which does not follow the curve C of the integrating responsive characteristic. Namely, there causes a problem that the optical transmission through the cell which rises in a selection time period attenuates in a non-selection time period, whereby the average transmittance level decreases and hence the contrast ratio also decreases. Hereinafter, such phenomenon is called the "relaxation" of liquid crystal.

The relaxation phenomenon causes a serious problem when the number of rows multiplexed (N) is several hundreds or more and a liquid crystal display element having a average response time of about 150 msec or lower is used. In particular, it is considerable when the multiplexing is conducted to a liquid crystal display element having a average response time of about 100 msec or lower.

In this specification, the average response time of a liquid crystal display element is defined as follows.

When a light transmission degree on the application of an OFF voltage at the time when a sufficient time has passed is represented as $T_{OFF}$, a light transmission degree on the application of an ON voltage is as $T_{ON}$, the time of switching from the OFF voltage to the ON voltage is as $t_1$, the time when the light transmittance degree T becomes $(T_{ON}-T_{OFF})\times 0.9 + T_{OFF}$ after the switching time is $T_2$, the time of switching from the ON voltage to the OFF voltage again is as $t_3$, and the time when the light transmission degree T becomes $(T_{ON}-T_{OFF})\times 0.1 + T_{OFF}$ after the second switching time is as $t_4$, the average response time $\tau$ is expressed as follows:

$$\tau = ((t_4 - t_3) + (t_2 - t_1))/2$$

In order to suppress the relaxation phenomenon, it is considered to utilize a method of increasing the frame frequency to thereby shorten time intervals between selection pulses. In this case, however, a time to select a single line electrode (a pulse width) is necessarily short, and therefore, the reaction of the liquid crystal molecules to the selection pulses is delayed. Accordingly, effect of increasing the contrast ratio of a display is not large.

Further, when the magnitude of a frequency for driving is large, the resistance value of the electrodes is not negligible, so that there causes brightness nonuniformity in a display between a signal inputting portion of an electrode and the other portion, or there causes brightness nonuniformity in a display because of a change of $V_{th}$ with frequency. For the above-mentioned reasons, it was difficult to use the fast response type liquid crystal display element for the purpose of displaying good images.

On the other hand, T. N. Ruckmongathan proposes a method called Improved Hybrid Addressing Technique wherein a plurality of row electrodes are selected simultaneously or as a batch to drive them (hereinafter, referred to as IHAT method) in order to reduce a driving voltage and to minimize brightness nonuniformity in a display (1988 Internal Display Research Conference). A summary of the driving method is as follows.

An N number of line electrodes are divided into a p number (p=N/M) of subgroups each consisting of an M number of line electrodes, and the M number of line electrodes are selected as a batch to drive them.

A display information of an optional row of column electrodes in a selected subgroup is represented by an M-bit code $[d_{KM+1}, d_{KM+2}, \ldots, d_{KM+M}]$; $d_{KM+j}=0$ or 1 (where 0 designates OFF and 1 designates ON, and k is an integer changeable from 0 to (p−1) in a selected subgroup).

A selection pattern for the line electrodes is expressed by M-bit code $(W_1, W_2, \ldots, W_Q)$ of $2^M(=Q)$ kinds, i.e., $[a_{KM+1}, a_{KM+2}, \ldots, a_{KM+M}]$; $a_{KM+j}=0$ or 1.

The driving is conducted as follows.

(1) A subgroup is selected as a batch.

(2) An M-bit code is selected as a selection pattern for the line electrodes.

(3) When the line electrodes which are not selected are connected to the ground, the line electrodes selected are applied with $-V_r$ for logic 0 and $+V_r$ for logic 1.

(4) A line electrode pattern for the selected subgroup and a data pattern are compared for each bit by using exclusive logical sum (exclusive OR) to thereby obtain a value of the exclusive logical sum of these data.

(5) A mismatch number i of the two patterns is obtained from the exclusive logical sum.

(6) When the mismatched number is i, a voltage applied to the column electrodes is selected to be $V_i$.

(7) The voltage applied to the column electrodes is determined independently by repeating the steps (4)–(6) in the matrix.

(8) The voltage is applied to the line electrodes and the column electrodes simultaneously during a time $T_R$.

(9) A selection pattern is newly selected for the line electrodes, and a voltage applied to the column electrodes is determined through the steps (4)–(6). In the same manner as above, the voltage is applied simultaneously to another line electrodes and column electrodes during a time $T_R$.

(10) A cycle is completed when a $2^M$ number of selection patterns are selected once for all subgroups.

(11) A display is refreshed by repeating continuously the cycle.

In particular, when equations:

$$V_i = V_0(M-2i)/M, \text{ and}$$

$$V_r = V_0 M^{\frac{1}{2}}/M$$

are selected, the ON/OFF ratio of root mean square (r.m.s.) value of voltage can be largest. In this case, the ratio of the root mean square voltage of ON and OFF is expressed by:

$$V_{ON}/V_{OFF} = ((N^{\frac{1}{2}}+1)/(N^{\frac{1}{2}}-1))^{\frac{1}{2}}$$

The value obtainable is equal to $V_{ON}/V_{OFF}$ which is obtainable by using the conventional optimized amplitude selection method. Further, the effective value of voltage at each operating portion in the matrix becomes uniform, whereby a uniform display can be obtained regardless of display patterns.

While the IHAT is effective for reducing the brightness nonuniformity of display, the number of time intervals to complete a cycle is long and hence is not suitable for gray shades using a technique similar to frame modulation. In this case, when the number of row electrodes selected is increased, the number of selection pulses required is sometimes increased as an exponential function. If the width of a selection pulse is uniform, a display requires a time $2^{M-1}/M$ times as much as the conventional method. For instance, if M=7, then 64/7, i.e. a time of 9.1 times is required.

It is an object of the present invention to eliminate the problems of the conventional driving method and to provide a new driving method for a liquid crystal display element.

In accordance with the present invention, there is provided a driving method of a matrix type liquid crystal display element comprising at least $J\times L$ number (J and L are respectively integers of 2 or more) of row electrodes and a plural number of column electrodes wherein, said $J\times L$ number of row electrodes are divided into a J number of row electrode subgroups each comprising an L number of row electrodes so that said subgroups are selected as each batch to be driven;

when voltages are applied to the row electrodes, either a voltage level of $+V_r$ or $-V_r$ (where $V_r>0$) is applied at a selection time, when a voltage at a nonselection time is 0 (zero);

voltages applied to the column electrodes are selected from an (L+1) number of voltage levels of $V_0$, $V_1, \ldots, V_L$ (where $V_0 < V_1 < \ldots < V_L$); and when a two-valued information of the j-th row electrode subgroup (j is an integer of any of 1 through J) in a specified column in the plural column electrodes is expressed by a column vector $D_j$ having an L number of elements (where the elements of the vector $D_j$ comprises 1 indicating ON and 0 indicating OFF), the following conditions are satisfied:

(1) said j-th row electrode subgroup is selected by applying sequentially voltages so that the elements of a selection voltage vector which constitute a row selection voltage, as defined in the following items (a) and (b), correspond to voltages to the row electrodes constituting the j-th line electrode subgroups:

(a) an orthogonal matrix $A = [\alpha_1, \alpha_2, \ldots, \alpha_q, \ldots, \alpha_k]$ (where $\alpha_q$ is a column vector having an L number of elements) comprising L rows and K columns, which has an element of $+V_r$ or $-V_r$ and in which the product of a matrix and a transposed matrix of the same assumes a scalar multiple of the unit matrix is selected (where K is an integer having a relation of $L \leq 2^p = K$ and p is a natural number), and (b) as said row selection voltage, a selection voltage vector which includes at least one of $\alpha_1, \alpha_2, \ldots, \alpha_k$, $-\alpha_1, -\alpha_2, \ldots, -\alpha_k$ is selected, and, (2) when said j-th row electrode subgroup is selected under the above-condition (1), the voltage applied to the column electrodes to indicate a display information by means of the vector $D_j$ are determined as in the following items (a) and (b):

(a) a vector $\beta$ is formed by the selection voltages applied to the j-th row electrode subgroup where $+V_r$ represents 1 and $-V_r$ represents 0, and (b) a voltage $V_i$ (i is an integer of any of 0 through L) given by the sum of exclusive OR of the elements corresponding to the vector $\beta$ and $D_j$ is applied to the column electrodes.

Further, it is an object of the present invention to provide a driving method of liquid crystal display element as described in the above wherein the display information of the j-th row electrode subgroup in a specified column of the plural column electrodes has a gradation of (U+1) stages (where U is a natural number of 2 or more) in place of the two-valued information; the selection vectors which constitute a row selection voltage comprise substantially each U number of $\alpha_1, \alpha_2, \ldots, \alpha_k, -\alpha_1, -\alpha_2, \ldots, -\alpha_k$ in which the selection voltage vectors are arranged in a row, are selected, and the selected vectors having the each U number are used to display a gradation display of (U+1) stages by giving a specified ratio to the total U number of ON and OFF signs.

In drawings:

FIG. 7 is graphs showing time sequential changes of voltages of a row electrode subgroup comprising $R_1-R_4$ in a case of applying the selection code shown in Table 4;

FIG. 9 is graphs showing voltages applied to column electrodes $C_1$, $C_2$, $C_3$, $C_9$ with the display pattern of FIG. 2 in a case of applying the selection code shown in Table 4;

Figure 1A:
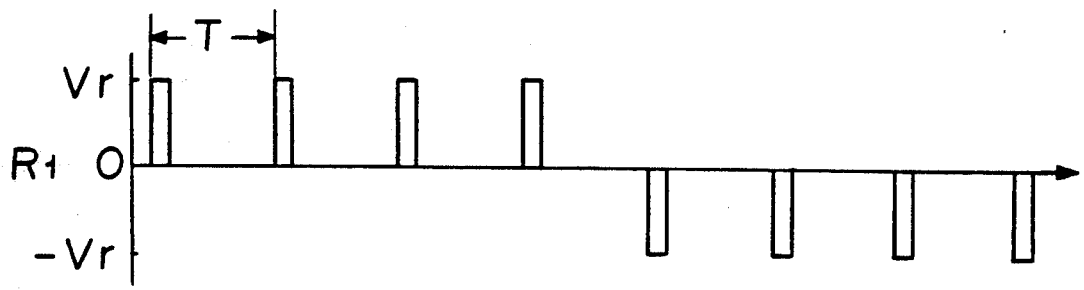
FIG. 1(a-d) is a graph showing time sequential changes of electric potential of a row electrode subgroup comprising $R_1-R_4$ in a case of applying the selection code shown in Table 1.
Figure 1B:
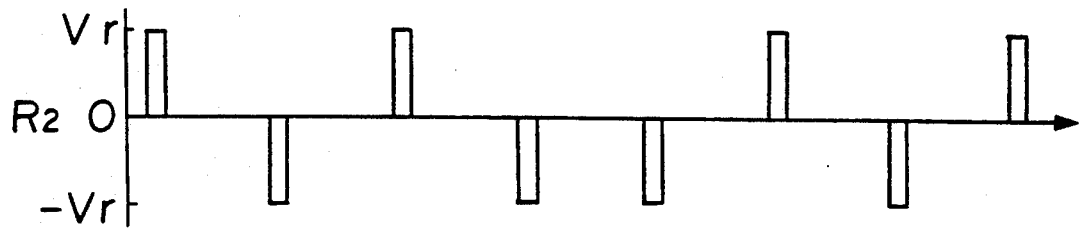
Figure 1C:
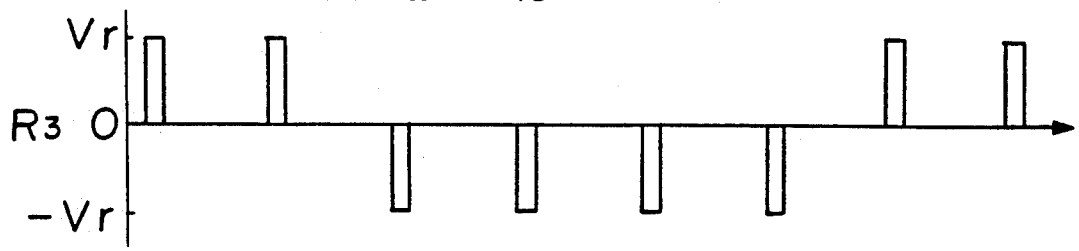
Figure 1D:
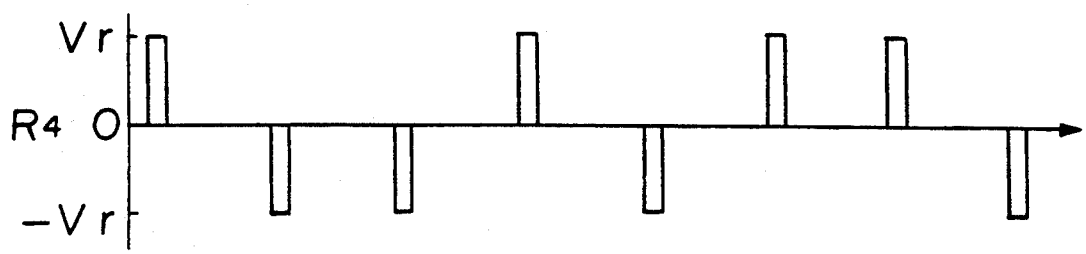

In the following, several embodiments of the present invention will be described in detail with reference to the drawings.

In the driving method according to the present invention, a plurality of row electrodes are selected as a batch in the same manner as the IHAT method. In this description, a group of row electrodes selected as a batch is called "a row electrode subgroup".

It is desirable that the number of row electrodes which constitute each of the row electrode subgroups is equal in order to simplify a driving circuit. However, since, in the construction of a typical cell, the total number of row electrodes is not equal to a multiple number of the row electrodes which constitute row electrode subgroups, it is sometimes impossible that the number of the row electrodes which constitute all row electrode subgroups is equal.

A case of driving row electrode subgroups each having an L number of row electrodes will be described (a case of driving row electrode subgroups in which some of row electrode subgroups have a fraction number of row electrodes will be also described).

In dividing the row electrodes into several row electrode subgroups, it is not always necessary to select adjacent row electrodes as a row electrode subgroup, but it is possible to select row electrodes at a position apart from another electrodes as a row electrode subgroup as far as there is no problem of wiring on a substrate.

In the present invention, it is preferable to use a fast response type liquid crystal display element. As described before, such fast response type liquid crystal display element can be obtained by reducing the thickness (d) of the liquid crystal layer and by using liquid crystal having a low viscosity and a large anisotropy of refractive index. As the liquid crystal having a large anisotropy of refractive index, a tolan type liquid crystal component is useful, such tolan type liquid crystal component being disclosed in, for instance, Japanese Unexamined Patent Publication No. 5631/1986. Further, there are liquid crystal having features as shown in Chemical Formulas 1.

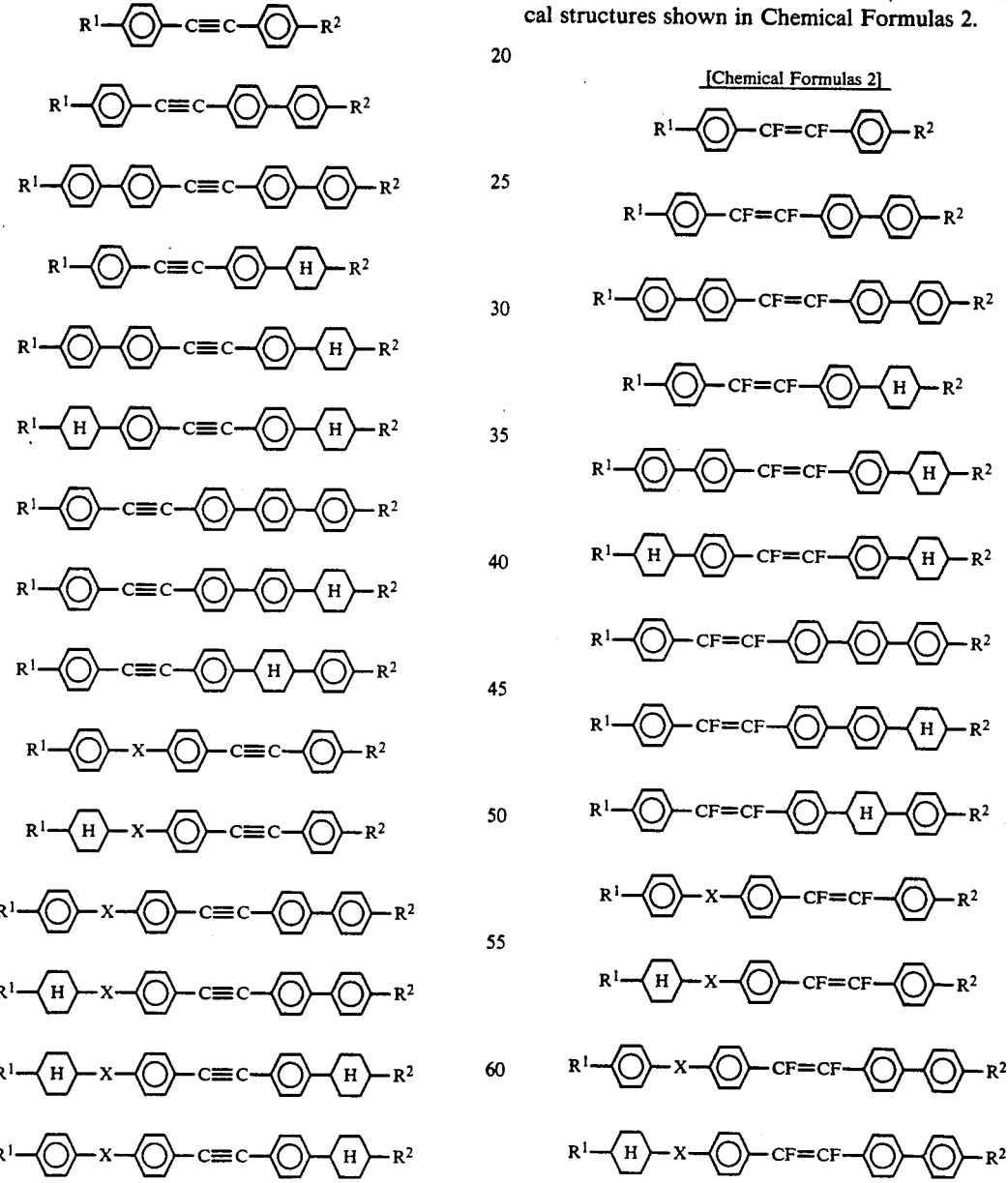

[Chemical Formulas 1]

In the above chemical formulas, —X— is —COO—, —OCO—, —CH$_2$CH$_2$— or —C≡C—; and R$^1$ and R$^2$ are independently a C$_1$-C$_{10}$ alkyl group, a halogen atom, a cyano group or a —SCN group, provided that when R$^1$ and R$^2$ have a carbon-carbon bond, an oxygen atom may be inserted between the carbon-carbon bond or between the carbon and an adjacent ring, or a part of the carbon-carbon bonds may be substituted by —COO—, —OCO— or —CH=CH—. These compounds are simply for illustration, but there may optionally be selected various other materials, the hydrogen atom of which may be substituted by a halogen atom, a cyano group, a methyl group or the like.

Further, as material having a large anisotropy of refractive index and a low viscosity, a difluorostilbene type liquid crystal is useful. As the difluorostilbene type liquid crystal, there are such liquid crystal components described in, for instance, Japanese Unexamined Patent Publication No. 96475/1989. Further, there are chemical structures shown in Chemical Formulas 2.

[Chemical Formulas 2]

-continued
[Chemical Formulas 2]

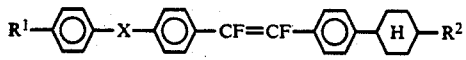

In the above chemical formulas, —X— is —COO—, —OCO—, —CH$_2$CH$_2$— or —C≡C—; and R$^1$ and R$^2$ are independently a C$_1$-C$_{10}$ alkyl group, a halogen atom, a —CN group or a —SCN group, provided that when R$^1$ and R$^2$ have a carbon-carbon bond, an oxygen atom may be inserted between the carbon-carbon bond or between the carbon and an adjacent ring, or a part of the carbon-carbon bonds may be substituted by —COO—, —OCO— or —CH=CH—. These compounds are simply for illustration, but there may optionally be selected various other materials, the hydrogen atom of which may be substituted by a halogen atom, a cyano group, a methyl group or the like.

The difluorostilbene type and the tolan type liquid crystal materials may be used separately or simultaneously. In particular, a liquid crystal composition containing 1-80% by weight of difluorostilbene, preferably 5-70% by weight, more preferably 10-60% by weight can greatly reduce the viscosity and can realize a fast response.

In the present invention, voltages to be applied to line electrodes are either a voltage level of $+V_r$ or $-V_r$ ($V_r>0$) in an selection time wherein voltages in a nonselection time is 0. In this case, the voltage of 0 in a non-selection time does not always mean grounding to the earth. A driving voltage to a liquid crystal element is determined by a voltage (a potential difference) applied between a line electrode and a column electrode. It is because a potential difference between the both electrodes is not changed by changing the potential of the both electrodes by the same quantity in parallel.

The voltages applied to a specified row electrode subgroup in a selection time can be expressed by vectors with L elements which are arranged time sequentially, the vectors having, as elements, voltages applied to each row electrodes. In this description, such matrices are called "selection voltage matrices", and the vectors which constitute the row select voltages are called "selection voltage vectors". Namely, if specified selection voltage matrices are determined, it is possible to select a row electrode subgroup in such a manner that the elements of the selection vectors which constitute the selection voltage matrices are made in correspondence to the voltages for each row electrodes, and the voltages corresponding to the selection voltage vectors which constitute the selection voltage matrices are sequentially applied to the row electrodes.

In the following, description will be made as to a method of forming the selection voltage matrices according to the present invention.

First of all, a matrix A of L rows and K columns: A=[α$_1$, α$_2$, ..., α$_q$, ..., α$_K$] (where α$_q$ is a column vector having an L number of elements) which has an element of $+V_r$ or $-V_r$ and in which the product of a matrix and a transposed matrix of the same assumes a scalar multiple of the unit matrix, is selected. In the matrix, K is an integer having a relation of L≦2$^p$=K, where p is a natural number. Describing specifically some examples, when L is 2, K is such that K=2(p=1), (p=2), 8(p=3), .... When L is 3 or 4, K assumes K=4, 8, 16, .... Further, when L is 5, 6, 7 or 8, K assumes K =8, 16, 32, .... However, when K is too large, the number of selection pulses necessary for the selection of line electrodes is also large. Accordingly, it is preferable that K assumes the smallest value among possible values.

Examples of the matrix A in which L =4, 8 and K =4, respectively, are shown in the following Lists 1.

[Lists 1]

$$V_r \cdot \begin{bmatrix} 1 & 1 & 1 & 1 \\ 1 & -1 & 1 & -1 \\ 1 & 1 & -1 & -1 \\ 1 & -1 & -1 & 1 \end{bmatrix} \quad (a)$$

$$V_r \cdot \begin{bmatrix} 1 & 1 & 1 & -1 \\ 1 & 1 & -1 & 1 \\ 1 & -1 & -1 & -1 \\ -1 & 1 & -1 & -1 \end{bmatrix} \quad (b)$$

$$V_r \cdot \begin{bmatrix} 1 & 1 & 1 & 1 & 1 & 1 & 1 & 1 \\ 1 & -1 & 1 & -1 & 1 & -1 & 1 & -1 \\ 1 & 1 & -1 & -1 & 1 & 1 & -1 & -1 \\ 1 & -1 & -1 & 1 & 1 & -1 & -1 & 1 \\ 1 & 1 & 1 & 1 & -1 & -1 & -1 & -1 \\ 1 & -1 & 1 & -1 & -1 & 1 & -1 & 1 \\ 1 & 1 & -1 & -1 & -1 & -1 & 1 & 1 \\ 1 & -1 & -1 & 1 & -1 & 1 & 1 & -1 \end{bmatrix} \quad (c)$$

As a result of practicing several kinds of matrices, and especially when the matrices described in the above Lists 1(a) and (c) which are called an Hadamard's matrix were used, it was found that an advantage was obtainable in reducing the brightness nonuniformity of display when liquid crystal elements were driven. In the case of L≠2$^p$, the above-mentioned L-lines-K columns matrix A can be formed by removing an optional (K−L) line from a K-rows matrix wherein the product of a matrix and a transposed matrix of the same forms a scalar multiple of the unit matrix. The following Lists 2 show examples of the martix A transformed from the 8-dimensional Hadamard's matrix shown in List 1(c), for instance.

[Lists 2]

$$V_r \cdot \begin{bmatrix} 1 & -1 & 1 & -1 & 1 & -1 & 1 & -1 \\ 1 & 1 & -1 & -1 & 1 & 1 & -1 & -1 \\ 1 & -1 & -1 & 1 & 1 & -1 & -1 & 1 \\ 1 & 1 & 1 & 1 & -1 & -1 & -1 & -1 \\ 1 & -1 & 1 & -1 & -1 & 1 & -1 & 1 \\ 1 & 1 & -1 & -1 & -1 & -1 & 1 & 1 \\ 1 & -1 & -1 & 1 & -1 & 1 & 1 & -1 \end{bmatrix} \quad (a)$$

$$V_r \cdot \begin{bmatrix} 1 & -1 & 1 & -1 & 1 & -1 & 1 & -1 \\ 1 & 1 & -1 & -1 & 1 & 1 & -1 & -1 \\ 1 & -1 & -1 & 1 & 1 & -1 & -1 & 1 \\ 1 & 1 & 1 & 1 & -1 & -1 & -1 & -1 \\ 1 & -1 & 1 & -1 & -1 & 1 & -1 & 1 \\ 1 & 1 & -1 & -1 & -1 & -1 & 1 & 1 \\ 1 & -1 & -1 & 1 & -1 & 1 & 1 & -1 \\ 1 & 1 & -1 & -1 & -1 & -1 & 1 & 1 \end{bmatrix} \quad (b)$$

List 2(a) shows a 7-row-8-column matrix formed by removing the first row from the matrix shown in List 1(c), and List 2 (b) is a 6-row-8-column matrix formed by removing the first and eighth rows from the matrix shown in List 1(c). In each of the matrices, the product of a matrix and a transposed matrix of the same assumes a scalar multiple of the unit matrix.

In the matrix A, each of the columns can be considered to be a single vector, whereby a formal expression of $A = [\alpha_1, \alpha_2, \ldots, \alpha_q, \ldots, \alpha_k]$ (where $\alpha_q$ is a column vector having an L number of elements) is made.

In the present invention, as the selection voltage matrices, matrices of vectors wherein the selection voltage vectors constituting the selection voltages are composed of at least $\alpha_1, \alpha_2, \ldots \alpha_K, -\alpha_1, -\alpha_2, \ldots, -\alpha_K$, and these selection voltage vectors are arranged in matrices are selected.

If two values (i.e. ON and OFF) are used for displaying information to be described, selection voltage matrices consisting of a 2K number of vectors wherein each of the vectors appears once in the selected voltage matrices can be selected.

However, it is not always necessary that the selection voltage matrices are formed by selecting each one among the 2K number of vectors, but it is possible to add another vector composed of $+V_r$ or $-V_r$ as an element, or an arrangement of a plurality of same vectors as far as effect by the present invention is not adversely affected. For instance, an arrangement of selection voltage matrices including all possible conditions of electric potential (in this case, the number of selection voltage vectors in the selection voltage matrices is $2^L$ or higher) can be considered. For instance, if a single row electrode subgroup is formed of four row electrodes, there are 16 kinds of possible conditions of electric potential ($2^4 = 16$). Namely, selection voltage matrix include 16 selection voltage vectors. Accordingly, the voltages corresponding to the selection voltage matrix form a row electrode selection waveform for the driving method of the present invention.

In the above method, each of the row electrode subgroups has all possible electric potential conditions, whereby brightness nonuniformity in a display can be effectively reduced. However, when the value L becomes large, the number of selection pulses required for the selection of row electrodes increases in a form of exponential function, and if the pulse width is unchanged, a time required for completing a single display cycle becomes extremely long. In this sense, it is most preferable to select selection voltage matrices wherein the selection voltage matrices constituting the selection voltage matrices are composed substantially of $\alpha_1, \alpha_2, \ldots \alpha_k, -\alpha_1, -\alpha_2, \ldots, -\alpha_k$, and the number of the selection voltage vectors constituting the selection voltage rows is substantially 2K. Thus, the number of selection pulses necessary to select the row electrodes can be minimized, which is most effective for a fast response display.

The above description concerns a binary (two-valued) display. However, it is possible to realize a gradation display by using a similar method.

The order of an arrangement of the selection voltage vectors which constitute the selection voltage matrices is optional, and it is possible to replace the arrangement of the selection voltage vectors for each subgroup or a display information. In order to reduce the brightness nonuniformity of display in actual driving methods, it is sometimes preferred to conduct such replacement.

Hereinbelow, for simplifying explanation, there will be used a pattern wherein $+V_r$ as an element of the selection voltage vectors is expressed as "1" and $-V_r$ is expressed as "0", which is called "a selection pattern". Further, an arrangement of several selection patterns in a time sequential form is called "a selection code".

Now, explanation is made as to use of selection voltage matrix (a selection code) suitable for driving fast response LCDs.

As a result of practically using several kinds of selection voltage matrices, it has been found it preferable in a view of reducing the brightness nonuniformity of display in liquid crystal display elements to carry out in such a manner that the number of selection voltage vectors in the selection voltage matrices is 2I (I is a natural number of $2I \geq 2K$), and the matrices consist of an I number of selection voltage vectors which form a former half portion and an I number of selection voltage vectors which form the later half portion wherein the former half and the latter half are the same in absolute value and opposite in positive and negative signs. Although the reason why the above-mentioned arrangement of vectors can reduce the brightness nonuniformity of display in driving the liquid display elements is not clear, it can be considered that a waveform of voltage resulted between electrodes in effecting a display exhibits a form of alternating voltage having a uniform frequency spectrum regardless of a display information. Hereinbelow, a selection code having such arrangement of the selection voltage vectors is called in particular "an inversion code".

Specifically describing, when a selection code consists of a 2I number of selection patterns, and there is considered two groups: a first group of the first - I th selection patterns and a second group of the (I+1)th - 2Ith selection patterns, a selection code wherein the content of the s th selection pattern and the content of the (s+I)th selection pattern are in a negative relation should be used. Namely, a row electrode selection code should be formed so as to satisfy the relation as shown in List 3 when the s th selection pattern is expressed as $W_s$.

[Lists 3]

$W_s = \overline{W_{s+I}}$ (s is an integer of 1 − I)

It was found for the inversion code to select rows of vectors having the order of $[\alpha_1, \alpha_2, \ldots \alpha_k, -\alpha_1, -\alpha_2, \ldots, -\alpha_k]$ in order to reduce the brightness nonuniformity of display when the selection voltage matrices are formed of a 2K number of selection voltage vectors.

Table 1 shows an example of selection code for row electrodes which is formed from a 4×4 Hadamard's matrix.

TABLE 1

| Selection pattern No. | 1 | 2 | 3 | 4 | 5 | 6 | 7 | 8 |
|---|---|---|---|---|---|---|---|---|
| Row electrode 1 | 1 | 1 | 1 | 1 | 0 | 0 | 0 | 0 |
| Row electrode 2 | 1 | 0 | 1 | 0 | 0 | 1 | 0 | 1 |
| Row electrode 3 | 1 | 1 | 0 | 0 | 0 | 0 | 1 | 1 |
| Row electrode 4 | 1 | 0 | 0 | 1 | 0 | 1 | 1 | 0 |

The selection code of Table 1 satisfies that the selection voltage matrices have the order of $[\alpha_1, \alpha_2, \ldots \alpha_k, -\alpha_1, -\alpha_2, \ldots, -\alpha_k]$. Further, selection codes shown in Tables 2 and 3 can be utilized in a case that a selection voltages (a selection pattern or patterns) are replaced for each subgroup. Numerical values in the Tables denote selection pattern number in Table 1. The selection patterns are applied to row electrodes time-sequentially from left to right. Table 2 shows that the selection patterns are changed after each row electrode subgroup has been selected. Table 3 shows that selection patterns are changed after every two row electrode subgroups are selected.

TABLE 2

| Subgroup No. 1 | 1 | 2 | 3 | 4 | 5 | 6 | 7 | 8 |
|---|---|---|---|---|---|---|---|---|
| Subgroup No. 2 | 2 | 3 | 4 | 5 | 6 | 7 | 8 | 1 |
| Subgroup No. 3 | 3 | 4 | 5 | 6 | 7 | 8 | 1 | 2 |
| Subgroup No. 4 | 4 | 5 | 6 | 7 | 8 | 1 | 2 | 3 |
| Subgroup No. 5 | 5 | 6 | 7 | 8 | 1 | 2 | 3 | 4 |

TABLE 3

| Subgroup No. 1 | 1 | 2 | 3 | 4 | 5 | 6 | 7 | 8 |
|---|---|---|---|---|---|---|---|---|
| Subgroup No. 2 | 1 | 2 | 3 | 4 | 5 | 6 | 7 | 8 |
| Subgroup No. 3 | 2 | 3 | 4 | 5 | 6 | 7 | 8 | 1 |
| Subgroup No. 4 | 2 | 3 | 4 | 5 | 6 | 7 | 8 | 1 |
| Subgroup No. 5 | 3 | 4 | 5 | 6 | 7 | 8 | 1 | 2 |

Table 4 shows an example of an arrangement of the selection voltage matrices containing all possible conditions of electric potential. In Table 4, a selection code arranged in the natural binary code is shown. Further, four row electrodes are designated as $a_1, a_2, a_3$ and $a_4$.

TABLE 4

| No. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| $a_1$ | 0 | 1 | 0 | 1 | 0 | 1 | 0 | 1 | 0 | 1 | 0 | 1 | 0 | 1 | 0 | 1 |
| $a_2$ | 0 | 0 | 1 | 1 | 0 | 0 | 1 | 1 | 0 | 0 | 1 | 1 | 0 | 0 | 1 | 1 |
| $a_3$ | 0 | 0 | 0 | 0 | 1 | 1 | 1 | 1 | 0 | 0 | 0 | 0 | 1 | 1 | 1 | 1 |
| $a_4$ | 0 | 0 | 0 | 0 | 0 | 0 | 0 | 0 | 1 | 1 | 1 | 1 | 1 | 1 | 1 | 1 |

In the case of Table 4, a random code or a gray code can be utilized other than the code according to the natural binary.

Further, a frequency equalizing code wherein a frequency of a row electrode selection waveform is equally applied to all row electrodes in a subgroup of the row electrodes. Table 5 shows an example of such frequency equalizing code wherein L=4.

TABLE 5

| No. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| $a_1$ | 0 | 1 | 1 | 1 | 1 | 0 | 1 | 1 | 0 | 0 | 1 | 0 | 1 | 0 | 0 | 0 |
| $a_2$ | 0 | 0 | 1 | 1 | 1 | 1 | 0 | 1 | 1 | 0 | 0 | 1 | 0 | 1 | 0 | 0 |
| $a_3$ | 0 | 0 | 0 | 1 | 1 | 1 | 1 | 0 | 1 | 1 | 0 | 0 | 1 | 0 | 1 | 0 |
| $a_4$ | 0 | 0 | 0 | 0 | 1 | 1 | 1 | 1 | 0 | 1 | 1 | 0 | 0 | 1 | 0 | 1 |

Table 6 shows an example of an inversion code formed of selection voltage matrices including all possible conditions of electric potential wherein L=3.

TABLE 6

| No. | 1 | 2 | 3 | 4 | 5 | 6 | 7 | 8 |
|---|---|---|---|---|---|---|---|---|
| $a_1$ | 0 | 1 | 0 | 1 | 1 | 0 | 1 | 0 |
| $a_2$ | 0 | 0 | 1 | 1 | 1 | 1 | 0 | 0 |
| $a_3$ | 0 | 0 | 0 | 0 | 1 | 1 | 1 | 1 |

In the above-inversion code, a negative form of the first - fourth line electrode selection patterns appears the 5th - 8th positions in that order.

On the other hand, if a display information is not constituted by using two values, but constituted by values which show a (U +1) stage gradation (U is an integer of 2 or more), an arrangement of the matrices of selection voltage vectors which constitute selection voltages, include at least each U×2K number of vectors among $\alpha_1, \alpha_2, \ldots, \alpha_k, -\alpha_1, -\alpha_2, \ldots, -\alpha_k$, is selected as the selection voltage matrices.

In the same manner as the case of using the two-valued displaying system, it is not always necessary that the section voltage matrices consist of each 2KU number of vectors, but it is possible to add another vector as an element consisting of $+V_r$ or $-V_r$, or to use an arrangement of a 2KU or more number of the same vectors, as far as the effect according to the present invention is not adversely affected.

Further, if the selection voltage matrices are substantially formed of each 2KU number of the above-mentioned vectors, the number of selection pulses necessary for selecting line electrodes can be reduced, which is preferred for a high speed driving. Particularly, when the selection voltage matrices are formed of only each 2KU number of the vectors, the number of selection pulses necessary for selecting line electrodes can be minimized to perform a high speed display.

The order of arrangement of the selection voltage vectors which constitute the selection voltage matrices is also optional. A random arrangement of the selection voltage vectors or the replacement of an arrangement of the selection voltage vectors for each subgroup or each display information may be used. It is often preferred to perform the above-mentioned rearrangement or replacement for driving a display element to thereby suppress unevenness of display, in the same manner as the case of using the two-valued display system.

In the (U+1) stage gradation display, also, various arrangements of the selection voltage vectors which constitute the selection voltage matrices can be utilized. For instance, there are an arrangement of [S, (S, ..., S, −S, −S, ..., −S] where a matrix of vectors $[\alpha_1, \alpha_2, \ldots, \alpha_k]$ is expressed as S so as to form a unit, or an arrangement of [S, −S, S, −S, ..., S, −S] may be utilized. In particular, it is preferable to use an arrangement of [S, S, ..., S, −S, −S, ..., −S] from the viewpoint of suppressing flicker.

In the following, description will be made as to a timing of applying to each row electrodes selection pulses corresponding to the selection voltage matrices mentioned above.

When a liquid crystal display element is driven to switch a pixel at a high speed, it is desirable to use fast response type liquid crystal display element in order to obtain a quick change in the transmission of light in the display element. In this case, there causes such a problem that the orientation of the liquid crystal molecules are relaxed when selection pulses are not applied to the liquid crystal molecules, as described before. Such problem becomes serious when the average response time of a liquid crystal display element is 150 msec or lower in a case that a multiplexing is conducted to the liquid crystal display element when the number of rows multiplexed is several hundreds or more. In particular, it is serious in a liquid crystal display element having an average response time of 100 msec or lower when it is subjected to multiplexing.

In order to suppress such relaxation of liquid crystal, it is preferred to change the length of the non-selection time period wherein no selection voltage is applied to row electrodes. Specifically, the change can be conducted according to the method of the present invention in such a manner of dispersively applying selection pulses during the scan period.

In accordance with this method, the voltages corresponding to the selection voltage matrices are not applied continuously to a single row electrode subgroup, but the scanning is divided into several stages in a manner that after selecting a row electrode subgroup, the next row electrode subgroup is selected.

Specifically, the following sequential steps are used.

A predetermined number of row select vectors are applied continuously to select each row electrode subgroup before selecting the next subgroup with the same number of row select vectors. A cycle is completed when all the subgroups have been selected using all the vectors in the row selection matrix once.

Thus, it is possible to change the length of the non-selection time period wherein a selection voltages are not applied to the row electrodes.

In the conventional optimized amplitude selective addressing method, two selection pulses having different polarity are applied to row electrodes during scanning so as to obtain d.c.-free operation of the display. Accordingly, two selection pulses are used in a cycle.

On the other hand, according to the present invention, the number of selection pulses corresponds to the number of stages by which the selection voltage matrices are splitted. Accordingly, when the selection voltage matrices are divided into three or more, the number of the selection voltage pulses appearing during scanning period can be much more than that of the conventional method.

Further, it is extremely preferable to equalize the number of selection voltage vectors included in each stage, which is not essential to the present invention although. However, it is effective to simplify the construction of the driving circuit.

The length of the non-selection time in which the selection voltages are not applied to the row electrodes can be changed according to the fast response characteristic of the liquid crystal display element. In general, an increase of the number of stages divided in the selection voltage matrices reduces the non-selection time, which is effective to suppress the relaxation phenomenon in liquid crystal display. In other words, if the number of selection pulses is increased by dividing, it is easy to maintain the light transmission through the cell to nearly a constant value. Accordingly, the most preferable way which can prevent the reduction of an average level of transmittance and the reduction of the contrast ratio is to give a single selection voltage vector in each stage.

For simplification, description will be made mainly as to the above-mentioned case.

In the present invention, the total number (N) of row electrodes are selected to perform a two-valued display to form several groups each having an L number of row electrodes, the minimum number of selection pulses to be applied to each row electrodes for a cycle is $2K \cdot (N/L)$, which is substantially equal to 2N in number in the conventional method. Accordingly, if the both methods have the same cycle time, the width of the selection pulses forming a selection pattern is the same between the both methods. On the other hand, in view of each of the row electrodes, the number of selection pulses applied to the row electrode for a display is 2L when $L = 2^p$ (p is an integer). If the total number (2L) of selection pulses are applied to the row electrodes in a dispersed form, a non-selection time wherein a no selection voltage is applied to the row electrodes can be reduced to 1/L in comparison with that by the conventional method. Namely, the feature of the method of the present invention is to increase the number of selection pulses without changing substantially the width of the selection pulses.

FIG. 1 shows row waveforms applied to certain row electrodes in accordance with the selection code shown in Table 1 wherein $R_1$-$R_4$ represent row electrodes, and a time interval T is a time interval between two row select pulses in a case that row electrodes having the total number N are divided into several row electrode subgroups each having an L number of row electrodes.

Figure 8A:
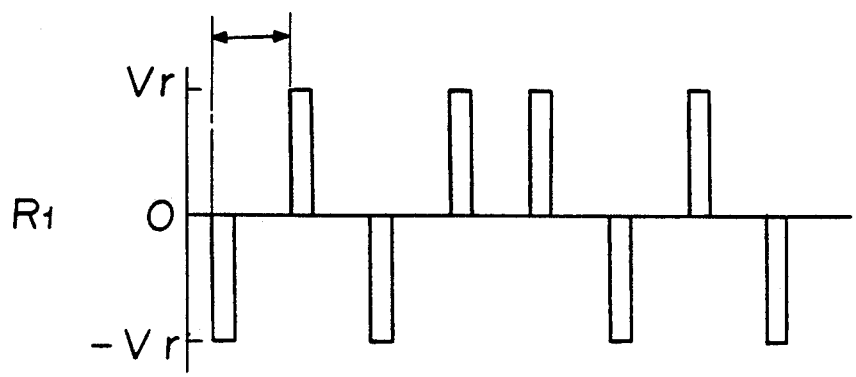
FIG. 8 is graphs showing time sequential changes of voltages of a row electrode subgroup comprising $R_1-R_3$ in a case of applying the selection code shown in Table 6.
Figure 8B:
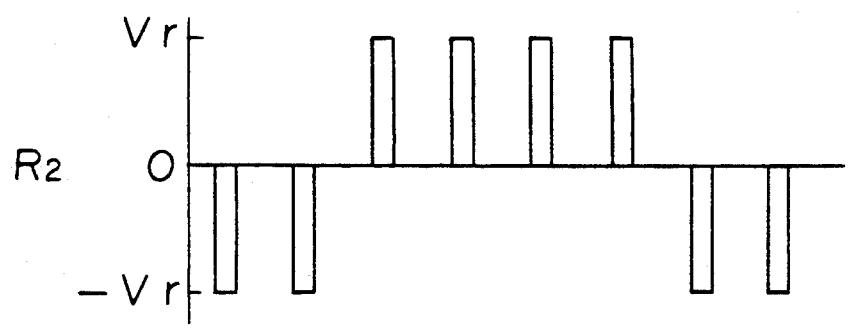
Figure 8C:
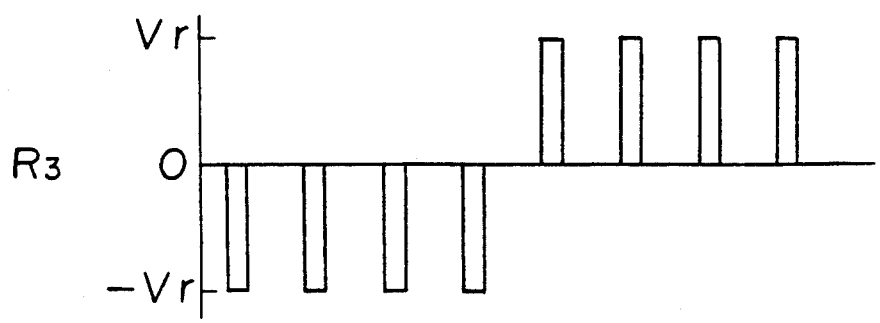

FIG. 7 shows row waveforms applied to a row electrode subgroup $R_1$-$R_4$ consisting of 4 row electrodes in accordance with the selection code shown in Table 4. As is clear from FIG. 7, it is understood that a selection pulse appears for each scan of 100 subgroups (i.e. scanning is conducted to 400 row electrodes). FIG. 8 shows time-sequentially changing voltages applied to a row electrode subgroup $R_1$-$R_3$ in accordance with the selection code shown in Table 6, which is shown in the same manner as FIG. 1. In this case, the total number of the line electrodes is N=240.

In the following, description will be made as to voltages applied to column electrodes to display a specified display information where a specified line electrode subgroup is selected under the condition as described above.

In the present invention, an (L+1) number of voltage levels are used, and voltages selected from the (L+1) number of voltages in accordance with a selection pattern for a line electrode subgroup are applied to column electrodes to drive them. As described before, since a voltage waveform should be in a form of alternating voltage in order to ensure a long life of the display, the (L+1) number of voltage levels preferably have voltages: $V_0, V_1, \ldots, V_L$ which satisfies at least the following condition: $V_0 < V_1 < \ldots < V_L$.

Selection of a voltage level among the above voltage levels is determined in consideration of a display information and selection voltages applied to the line electrodes. A method of determination of a suitable voltage level will be explained later.

Since the voltage waveform is preferably in a form of alternating voltage, $V_i$ is determined as $V_L - i$. It is possible to shift the voltages applied to the row electrodes and the column electrodes by the same amount together since there is no net change of electric potential difference between these electrodes.

Further, the absolute value of each of the voltage levels $V_0, V_1, \ldots, V_L$ should be determined depending on the construction of a liquid crystal display element and other factors.

In the following, selection of a voltage to be applied to electrodes from the (L+1) number of voltage levels wherein a specified display pattern is provided, will be described.

Figure 2:
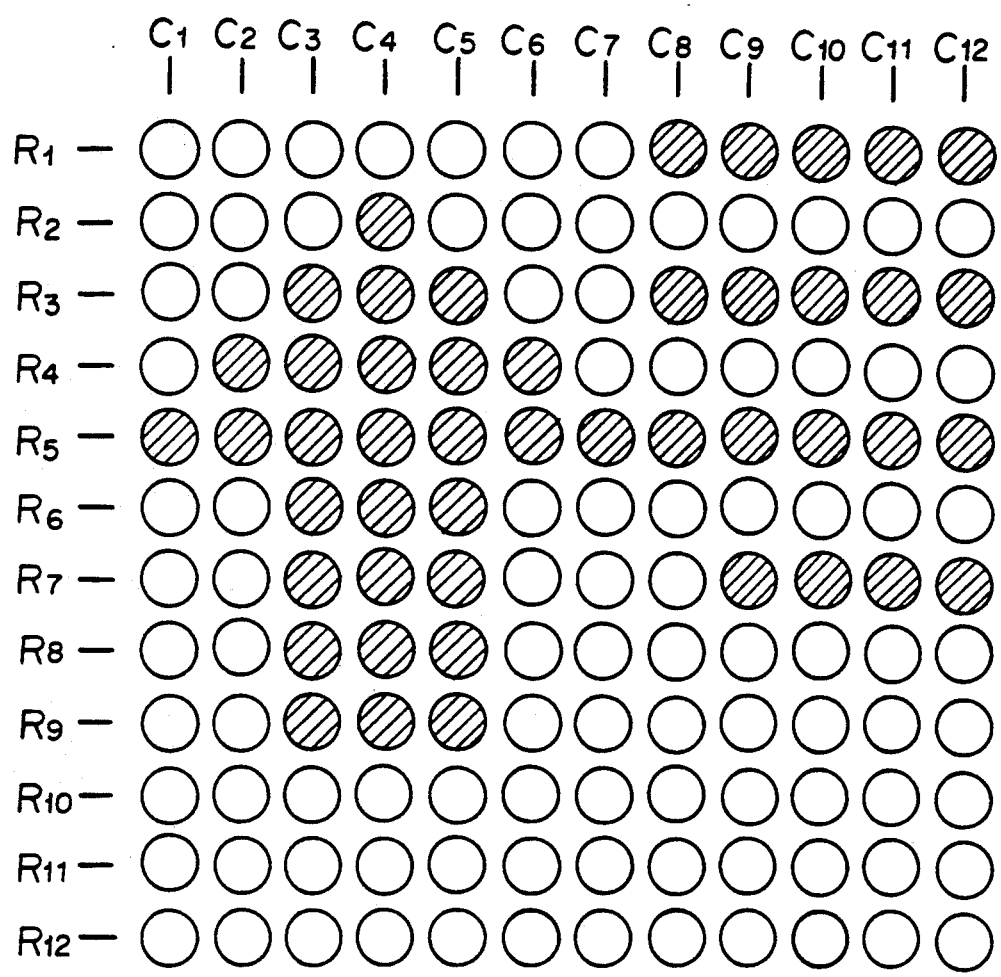
FIG. 2 is a diagram showing a display pattern for a liquid crystal display element.
Figure 3A:
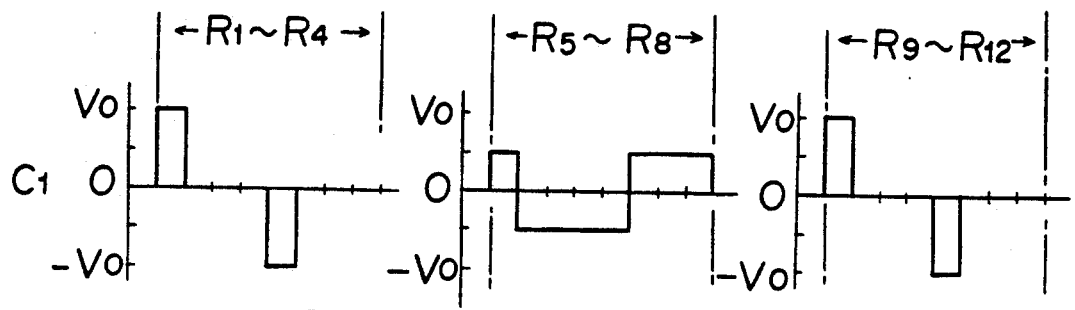
FIG. 3 is a graph showing changes of voltages applied to column electrodes $C_1$, $C_2$, $C_3$, $C_9$ with the display pattern shown in FIG. 2 in a case of applying the selection code shown in Table 1.
Figure 3B:
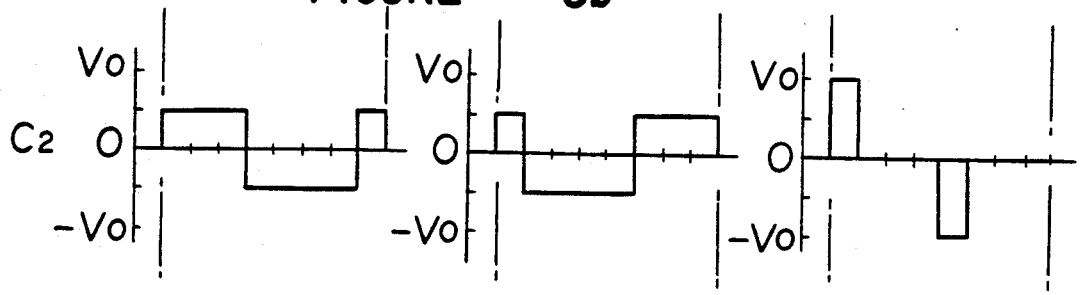
Figure 3C:
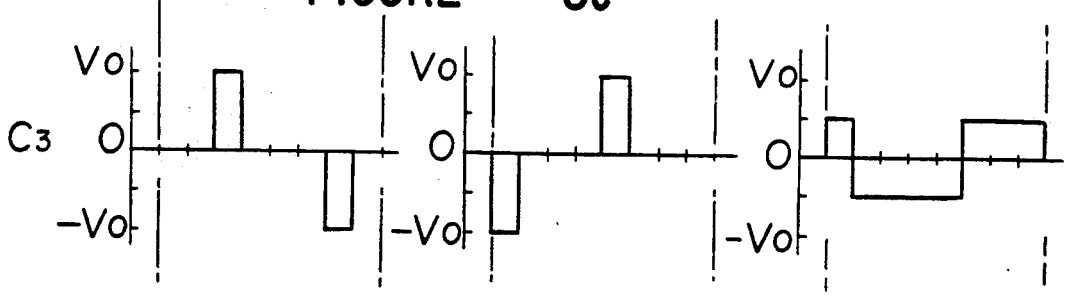
Figure 3D:
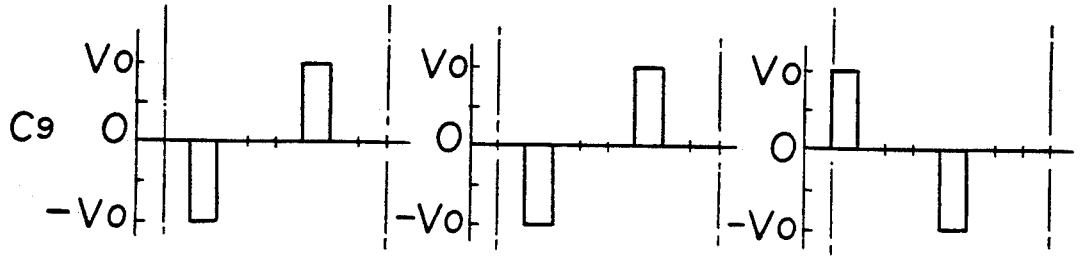

First of all, in a case that a display information is constituted by a two-valued system will be described. FIG. 2 shows a part of a display pattern, as a form of model, of a matrix having 400 row electrodes. Data in a Table which is shown in the lower part of FIG. 2 correspond to the display pattern of the matrix in the upper part of FIG. 2 wherein ON represents 1 and OFF represents 0. When 4 row electrodes are selected as a batch, the data in the column electrodes are divided into several subgroups, each consisting of 4-bit data patterns. The display data of jth row electrode subgroup (j is an integer having 1−J) is expressed by a column vector $D_j$ having 4 number of elements (where the elements of the vector $D_j$ consist of 1 representing ON and 0 representing OFF). For instance, the column vector of the column electrode $C_9$ is $D_1 = t(d_1, d_2, d_3, d_4) = t(1, 0, 1, 0)$ where t represents transposition.

For determining a voltage applied to a column electrode, vectors ($\beta$) of a selection pattern of selection voltages applied to the row electrodes and vectors of a display data for the column electrodes are used and exclusive OR is applied to each elements corresponding to these vectors to thereby obtain the sum. For instance, when the selection voltages of the first subgroup of the row electrodes in FIG. 2 are expressed by a selection patter of [1,1,1,1], voltages to be applied to the column electrode $C_9$ in FIG. 2 is determined. Then, the sum of the exclusive OR operation is expressed by List 4.

[Lists 4]
$$i = (1 \cdot 1 + 1 \cdot 1) + (0 \cdot 1 + 0 \cdot 1) + (1 \cdot 1 + 1 \cdot 1) +$$
$$(0 \cdot 1 + 0 \cdot 1) = 0 + 1 + 0 + 1 = 2$$

The voltage level to be applied to the electrode is expressed by $V_i$ when i is obtained.

For instance, Table 1 is selected for the selection code for the row electrodes. In a case of displaying the display pattern shown in FIG. 2 voltages applied to the column electrodes $C_1, C_2, C_3$ and $C_9$ are shown in FIG. 3. In FIG. 3, an area indicated $R_1$-$R_4$ means an area showing a change of voltage in a time period in which the row electrode subgroup $R_1$-$R_4$ is selected. In FIG. 3, each area $R_1$-$R_4$, $R_5$-$R_8$ or $R_9$-$R_{12}$ is independently depicted. Further, for easy view, the time axes (abscissa) is shown by eliminating selection time periods of other subgroups. Therefore, it should be understood that when selection pulses are dispersively applied to the electrodes, the voltages are not continuously applied. Namely, there is an application of a voltage as shown in FIG. 2, and, then, voltage applications are conducted to other row electrode subgroups, and after a time of the voltage application to the other line electrode subgroups has passed, a next voltage application is conducted.

When the maximum value of column electrode voltage is $V_c$ and if $V_i = V_c (2_i - L)/L$ and $V_r = V_c N^{\frac{1}{2}}/L$ (where N is the total number of line electrodes) are selected, $V_{ON}/V_{OFF}$ of the effective value of voltage can be preferably maximized. Further, it is possible to adjust the levels of $V_r$ and $V_i$ so as to obtain a desired contrast ratio near the value regardless of the above-mentioned conditions.

Figure 4A:
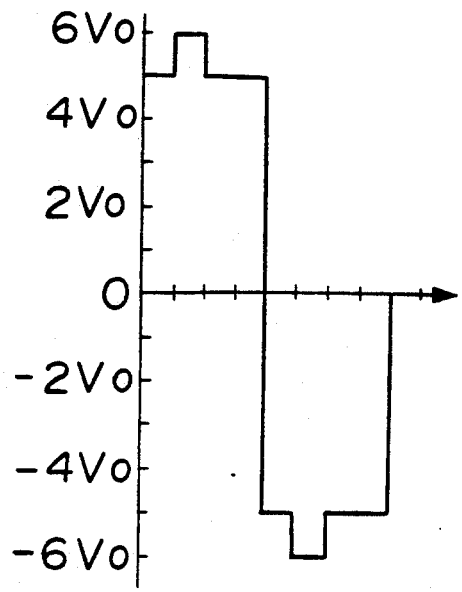
FIG. 4 is graphs showing voltages applied to the electrodes $R_1-C_9$ and $R_2-C_9$ with the display pattern of FIG. 2 in a case of applying the selection code shown in Table 1.
Figure 4B:
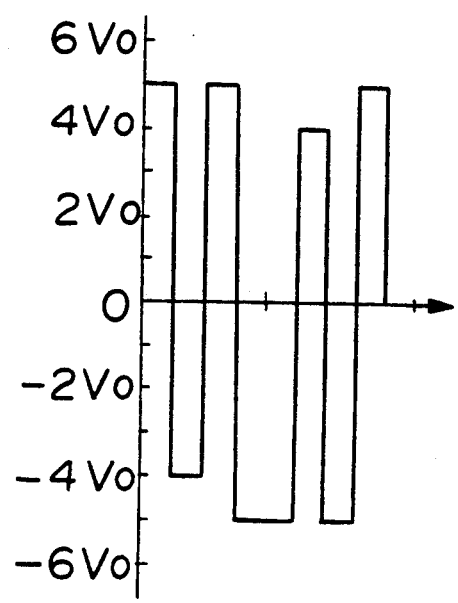
Figure 5A:
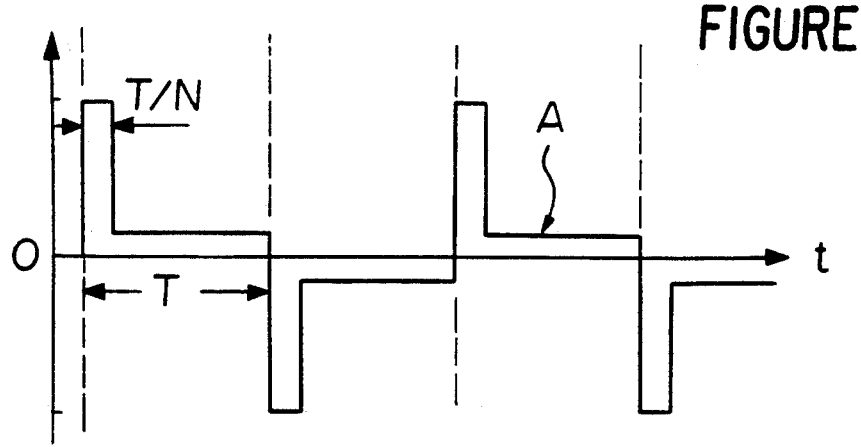
FIG. 5(a-b) is graphs showing an integrating response characteristic and a relaxation phenomenon.
Figure 5B:
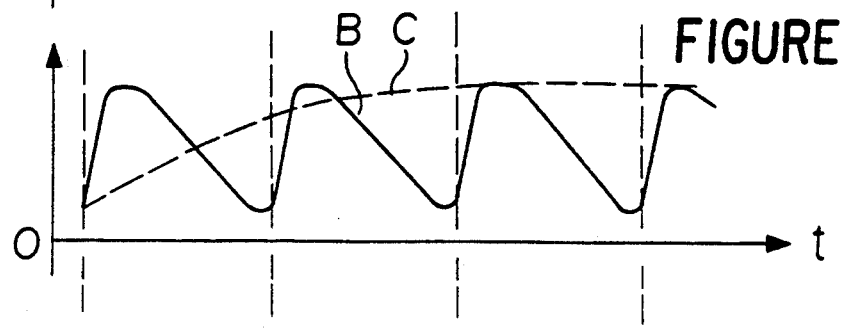

In FIG. 2, when L=4, a group of $V_4 = +V_c$, $V_3 = +V_c/2$, $V_2 = 0$, $V_1 = -V_c/2$ and $V_0 = -V_c$ may be selected. Further, $V_r = 5V_c$ under the above-mentioned conditions. FIG. 4 shows a change of voltage of $R_1$-$C_9$ (an ON state) and $R_2$-$C_9$ (an OFF state) in FIG. 2 in such case wherein the time axes (abscissa) is depicted by removing selection time periods for other subgroups for easy view in the same manner as FIG. 3.

When a display information is displayed and attention is paid to a specified line electrode subgroup, it is sometimes effective to reduce the brightness nonuniformity of display by changing an arrangement of the selection voltage rows (selection pattern) each time when one or a plurality of displays are finished. In particular, it is preferable to reduce the brightness nonuniformity of display by using such a technique that the selection voltages applied to each line of the line electrodes are substituted for those applied to the corresponding line electrodes in a specified subgroup. Namely, a matrix which is formed by replacing a line electrodes in a matrix A used for forming the selection voltage rows for a former display information, is used again as a matrix A for forming selection voltage rows.

Specifically, when the selection code shown in Table 1 is used for the first time, the selection codes as shown in Tables 7, 8 and 9 may be used subsequently each time a display information is changed. The selection code of each Table is formed by shifting the selection voltages applied to respective line electrodes.

TABLE 7

| Selection pattern No. | 1 | 2 | 3 | 4 | 5 | 6 | 7 | 8 |
|---|---|---|---|---|---|---|---|---|
| Row electrode 1 | 1 | 0 | 1 | 0 | 0 | 1 | 0 | 1 |
| Row electrode 2 | 1 | 1 | 0 | 0 | 0 | 0 | 1 | 1 |
| Row electrode 3 | 1 | 0 | 0 | 1 | 0 | 1 | 1 | 0 |
| Row electrode 4 | 1 | 1 | 1 | 1 | 0 | 0 | 0 | 0 |

TABLE 8

| Selection pattern No. | 1 | 2 | 3 | 4 | 5 | 6 | 7 | 8 |
|---|---|---|---|---|---|---|---|---|
| Row electrode 1 | 1 | 1 | 0 | 0 | 0 | 0 | 1 | 1 |
| Row electrode 2 | 1 | 0 | 0 | 1 | 0 | 1 | 1 | 0 |
| Row electrode 3 | 1 | 1 | 1 | 1 | 0 | 0 | 0 | 0 |
| Row electrode 4 | 1 | 0 | 1 | 0 | 0 | 1 | 0 | 1 |

TABLE 9

| Selection pattern No. | 1 | 2 | 3 | 4 | 5 | 6 | 7 | 8 |
|---|---|---|---|---|---|---|---|---|
| Row electrode 1 | 1 | 0 | 0 | 1 | 0 | 1 | 1 | 0 |
| Row electrode 2 | 1 | 1 | 1 | 1 | 0 | 0 | 0 | 0 |
| Row electrode 3 | 1 | 0 | 1 | 0 | 0 | 1 | 0 | 1 |
| Row electrode 4 | 1 | 1 | 0 | 0 | 0 | 0 | 1 | 1 |

A typical driving method of the present invention to display a two-valued display information will be described wherein the number of row electrodes selected as a batch is 4 (L=4), and the number of line electrode subgroups is J.

A basic selection code is previously determined. The selection code shown in Table 1 is used here.

First, the selection pattern number 1 of Table 1 is applied to the first row electrode subgroup. At the same time, voltages determined from this selection pattern and display data are applied to each and every column electrode. Then, the selection pattern number 2 of Table 1 is applied to the second line electrode subgroup. At the same time, this selection pattern and voltages determined from the second selection pattern and display data are applied to every column electrodes. Then, the selection pattern number 3 of Table 1 is applied to the third row electrode subgroup. Each of the row electrodes and column electrodes are applied with the voltages in the same manner as above. The above-mentioned steps are repeatedly conducted to the subsequent row electrode subgroups until the J th subgroup.

Then, the selection pattern number 2 of Table 1 is applied to the first row electrode subgroup. Then, the selection pattern number 3 of Table 1 is applied to the second row electrode subgroup. These steps are repeatedly conducted to the subsequent subgroups until the J th subgroup.

Thus, the selection patterns of Table 1 are sequentially applied to each of the row electrode subgroups until all patterns are applied, whereby a display is completed.

In the next cycle, the selection code of Table 7 is used which is formed by interchanging the rows of Table 1.

In the subsequent cycle, the selection code of Table 8 is used. Then, in the next cycle, the selection code of Table 9 is used. After this operation, the selection code of Table 1 is used. Thus, the selection codes are sequentially used in successive cycles.

For instance, when the display pattern of FIG. 2 is to be displayed and if the selection code of Table 4 is selected, voltages applied to column electrodes $C_1$, $C_2$, $C_3$, $C_9$ are as in FIG. 9. In FIG. 9, an area $R_1$-$R_4$ represents a time period in which a row electrode subgroup $R_1$-$R_4$ is selected. The area $R_1$-$R_4$ and other areas $R_5$-$R_8$ and $R_9$-$R_{12}$ are shown independently. For easy view, the time axes (abscissa) are depicted without showing time periods for selecting other subgroups. Therefore, in the present invention, when the selection pulses are applied dispersively, voltages are not continuously applied. Namely, after a voltage is applied as shown in FIG. 9, voltages are applied to other row electrode subgroups. When a time necessary for applying the voltages to other subgroups has passed, another voltage is applied as shown in the figure. This is conducted in the same manner as FIG. 3.

Figure 10A:
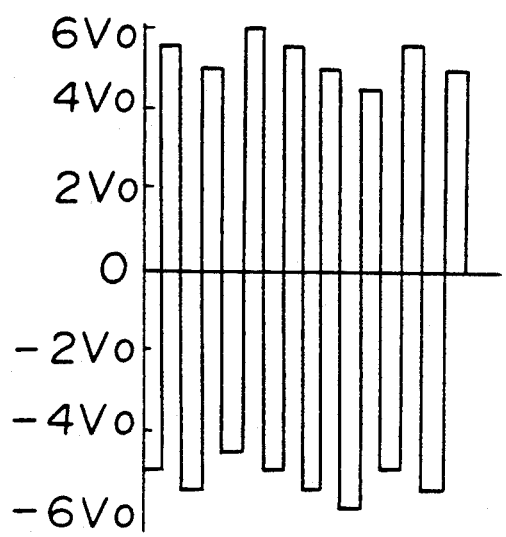
FIG. 10 is graphs showing voltages applied to the electrodes $R_1-C_9$ and $R_2-C_9$ with the display pattern of FIG. 2 in a case of applying the selection code shown in Table 4.
Figure 10B:
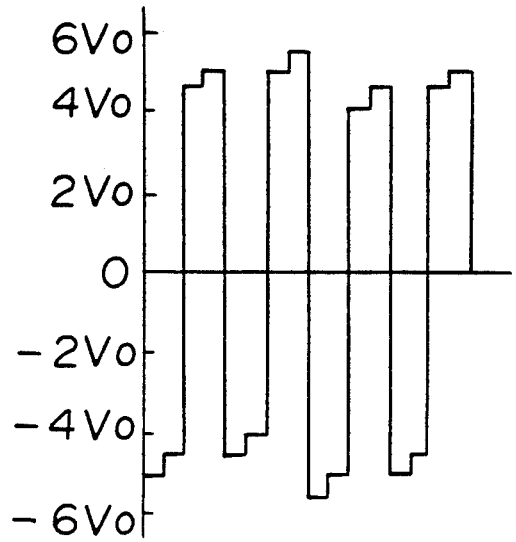
Figure 11A:
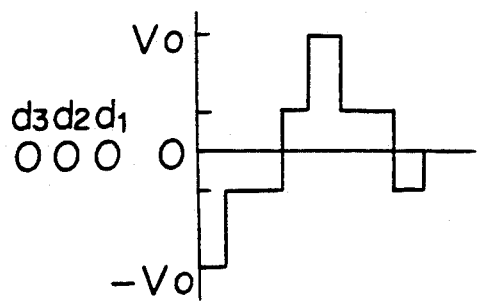
FIG. 11 is graphs showing voltage waveforms applied to column electrodes with display patterns in a case of applying selection code shown in Table 6.
Figure 11B:
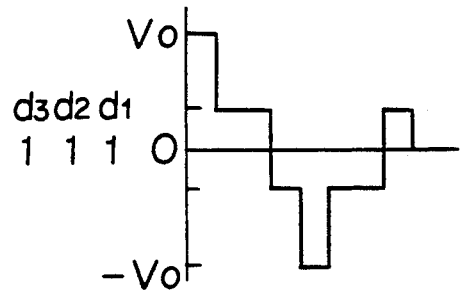
Figure 11C:
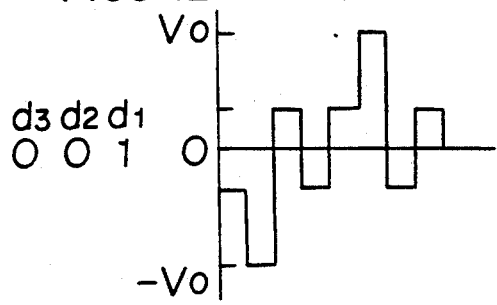
Figure 11D:
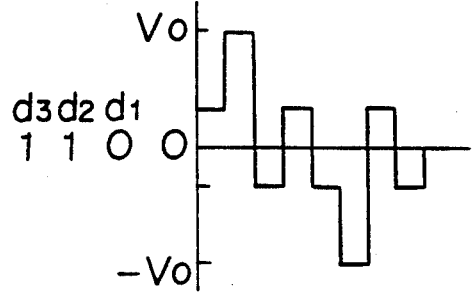
Figure 11E:
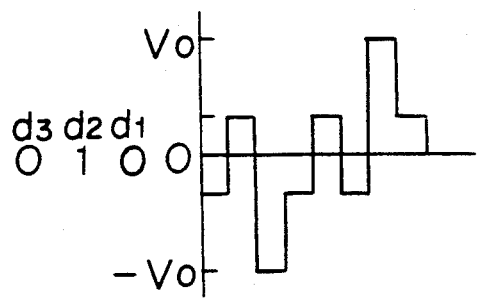
Figure 11F:
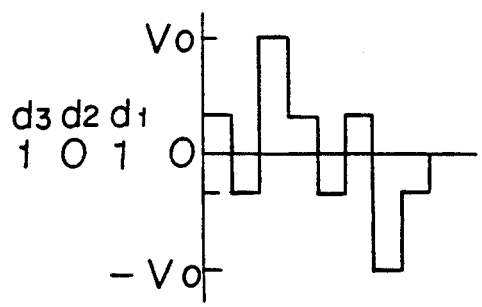
Figure 11G:
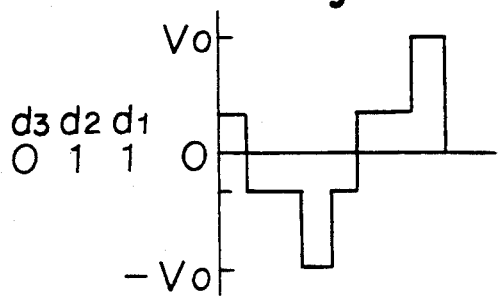
Figure 11H:
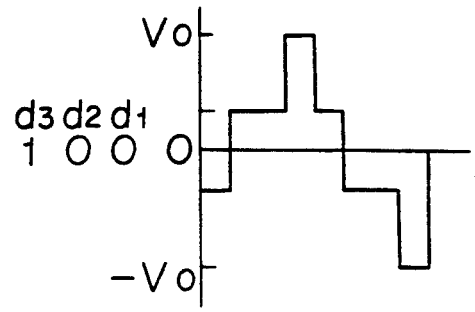
Figure 12A:
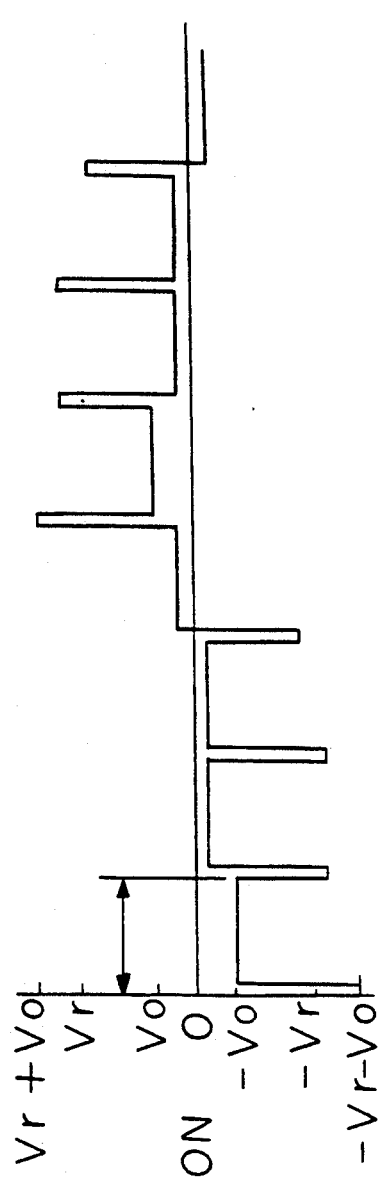
FIG. 12 is graphs showing waveforms of the difference of electric potential between the electrode $R_3$ shown in FIG. 8 and an optional column electrode in cases of the entirely ON and OFF.
Figure 12B:
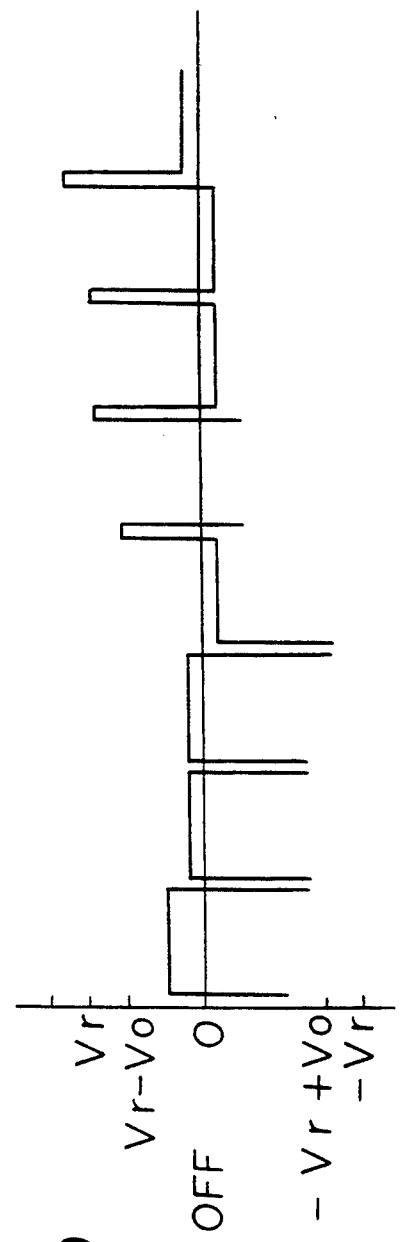

FIG. 10 shows a change of voltage with respect to $R_1$-$C_9$ (an ON state) and $R_2$-$C_9$ (an OFF state) in FIG. 2 wherein in the above mentioned conditions, the voltage levels are selected as $V_4=+V_c$, $V_3=+V_c/2$, $V_2=0$, $V_1=-V_c/2$ and $V_0=-V_c$, and $V_4=5V_c$ is selected. In the same as FIG. 9, the time axes (abscissa) are depicted by omitting time periods for selecting other 99 subgroups which is in a non-selection state, in FIG. 7.

The following description concerns a case of selecting the selection code shown in Table 6.

As shown in Table 4, all possible states in the data patterns $D=t(d_1, d_2, d_3)$ in a row electrode subgroup with respect to a single row of column electrodes are 8. An optional display pattern can be formed by the combination of 8 states.

Table 10 shows a result obtained by the calculation of a formula: $V_i = -V_0(2i-L)/L$, wherein i is the sum of exclusive OR for each bit of the line electrode selection patterns and the data patterns, and $V_i$ corresponds to i, and the values of $V_i$ are expressed only by coefficients of $V_0$.

TABLE 10

| C  $d_3$ | 0 | | 0 | | 0 | | 0 | | 1 | | 1 | | 1 | | 1 | |
|---|---|---|---|---|---|---|---|---|---|---|---|---|---|---|---|---|
| C  $d_2$ | 0 | | 0 | | 1 | | 1 | | 1 | | 1 | | 0 | | 0 | |
| R  $d_1$ | 0 | | 1 | | 0 | | 1 | | 1 | | 0 | | 1 | | 0 | |
| $a_3 a_2 a_1$ | i | $V_i$ | i | $V_i$ | i | $V_i$ | i | $V_i$ | i | $V_i$ | i | $V_i$ | i | $V_i$ | i | $V_i$ |
| 000 | 0 | $-1$ | 1 | $-\frac{1}{3}$ | 1 | $-\frac{1}{3}$ | 2 | $\frac{1}{3}$ | 3 | 1 | 2 | $\frac{1}{3}$ | 2 | $\frac{1}{3}$ | 1 | $-\frac{1}{3}$ |
| 001 | 1 | $-\frac{1}{3}$ | 0 | $-1$ | 2 | $\frac{1}{3}$ | 1 | $-\frac{1}{3}$ | 2 | $\frac{1}{3}$ | 3 | 1 | 1 | $-\frac{1}{3}$ | 2 | $\frac{1}{3}$ |
| 010 | 1 | $-\frac{1}{3}$ | 2 | $\frac{1}{3}$ | 0 | $-1$ | 1 | $-\frac{1}{3}$ | 2 | $\frac{1}{3}$ | 1 | $-\frac{1}{3}$ | 3 | 1 | 2 | $\frac{1}{3}$ |
| 011 | 2 | $\frac{1}{3}$ | 1 | $-\frac{1}{3}$ | 1 | $-\frac{1}{3}$ | 0 | $-1$ | 1 | $-\frac{1}{3}$ | 2 | $\frac{1}{3}$ | 2 | $\frac{1}{3}$ | 3 | 1 |
| 111 | 3 | 1 | 2 | $\frac{1}{3}$ | 2 | $\frac{1}{3}$ | 1 | $-\frac{1}{3}$ | 0 | $-1$ | 1 | $-\frac{1}{3}$ | 1 | $-\frac{1}{3}$ | 2 | $\frac{1}{3}$ |
| 110 | 2 | $\frac{1}{3}$ | 3 | 1 | 1 | $-\frac{1}{3}$ | 2 | $\frac{1}{3}$ | 1 | $-\frac{1}{3}$ | 0 | $-1$ | 2 | $\frac{1}{3}$ | 1 | $-\frac{1}{3}$ |
| 101 | 2 | $\frac{1}{3}$ | 1 | $-\frac{1}{3}$ | 3 | 1 | 2 | $\frac{1}{3}$ | 1 | $-\frac{1}{3}$ | 2 | $\frac{1}{3}$ | 0 | $-1$ | 1 | $-\frac{1}{3}$ |
| 100 | 1 | $-\frac{1}{3}$ | 2 | $\frac{1}{3}$ | 2 | $\frac{1}{3}$ | 3 | 1 | 2 | $\frac{1}{3}$ | 1 | $-\frac{1}{3}$ | 1 | $-\frac{1}{3}$ | 0 | $-1$ |

Based on Table 10, voltage waveforms to be applied to a row of column electrodes in a time period of selecting a subgroup is determined, which is shown in FIG. 11. An optional display is obtainable by the combination of 8 kinds of waveforms in FIG. 11.

In particular, in view of a data pattern of entirely ON (($d_1$, $d_2$, $d_3$)=(1, 1, 1)) and a data pattern of entirely OFF (($d_1$, $d_2$, $d_3$)=(0, 0, 0)) with respect to a voltage waveform applied to $R_3$ in FIG. 8, it is found that the same voltage is always applied after 4 stages. This is also applicable to data patterns other than the data patterns of entirely ON and OFF.

Namely, by using the inversion code which is obtained by rearranging the above-mentioned data, as a selection code, it is possible that electric potentials having the same absolute value are repeated twice in a time period for scanning a picture surface (hereinbelow, it is referred to as a frame period or a frame frequency as the reciprocal number of it).

When a display is turned to ON, the application of a voltage of $+(V_r+V_c)$ and a voltage $-(V_r+V_c)$ each having the greatest absolute value is most effective for the movement of the liquid crystal molecules. In this case also, the voltages correctly appear once in 4 stages, i.e. at a frequency twice of the frame frequency.

Namely, in the conventional optimized amplitude selective addressing method, the frequency in the optical response of the liquid crystal is equal to the frame period, however, the frame frequency can be substantially twice when the inversion code is used as a selection code in the driving method of the present invention. Accordingly, brightness in an ON state and the contrast ratio can be increased. Further, in any display pattern, the optical response period of the liquid crystal is constant, whereby a uniform display can be obtained.

When a display information is not shown by two values, but has a gradation degree having (U+1) stages (U is an integer of 2 or more), a display can be obtained in substantially the same manner as the case of two-valued display. In this case also, rows of vectors are selected as selection voltage matrices wherein the selection voltage vectors which constitute the selection voltage matrices are respectively composed substantially of 2KU number of the vectors among $\alpha_1, \alpha_2, \ldots, \alpha_k, -\alpha_1, -\alpha_2, \ldots, -\alpha_k$, and the selection voltage vectors are arranged in series.

The (U+1) stage gradation display can be performed by displaying the signs of ON and OFF having a U number in total at a predetermined ratio with respect to the selection voltage vectors each composed of a U number.

A case that L=K=4 and a display having 4 degrees of gradation is performed, will be described. A selection code to be used is such one as shown in Table 11 which can be formed from a 4×4 Hadamard's matrix. In Table 11, the selection patterns are used from left to right. Further, each line of data arranged in the vertical direction corresponds to each row of row electrodes.

TABLE 11

| Row 1 | 1111 | 1111 | 1111 | 0000 | 0000 | 0000 |
|---|---|---|---|---|---|---|
| Row 2 | 1010 | 1010 | 1010 | 0101 | 0101 | 0101 |
| Row 3 | 1100 | 1100 | 1100 | 0011 | 0011 | 0011 |
| Row 4 | 1001 | 1001 | 1001 | 0110 | 0110 | 0110 |

Or, the selection code may be such as one as shown in Table 12.

TABLE 12

| Row 1 | 1111 | 0000 | 1111 | 0000 | 1111 | 0000 |
|---|---|---|---|---|---|---|
| Row 2 | 1010 | 0101 | 1010 | 0101 | 1010 | 0101 |
| Row 3 | 1100 | 0011 | 1100 | 0011 | 1100 | 0011 |
| Row 4 | 1001 | 0110 | 1001 | 0110 | 1001 | 0110 |

In the above Tables, the same kind of patterns appear three times. A gradation display can be obtained by assigning the three selection patterns to ON or OFF. For instance, the data having two ONs and an OFF corresponds to the second degree of gradation from the ON side. Further, the data having an ON and two OFFs corresponds to the third degree of gradation from the ON side. The assignment of ON and OFF should be uniform to obtain good appearance.

In the following, a case that a row electrode subgroups consists of an $L_r$ number of row electrodes which is smaller than an L number of row electrodes which constitute another row electrode subgroup, will be described. It is assumed that a $(L-L_r)$ number of row electrodes are added, whereby the total number of the row electrodes which constitute the regular row electrode subgroup is L. The row electrode subgroup is driven by applying voltages to the row electrodes and the column electrodes in the same manner as driving the regular row electrode subgroup. Specifically, when the subgroup consisting of an $L_r$ number of row electrodes is driven, it is assumed that there are a $(L-L_r)$ number of row electrodes which correspond to the $L_r$th, the $(L_r+1)$th, ..., the L th row electrodes, and display data for the assumed row electrodes are also prepared imaginarily. The display data may be formed of 0 or 1 in a two-valued display. The display data may be any degrees of gradation in a gradation display.

For instance, when a row-electrode subgroup of L=4 and $L_r$=3 is driven, three row electrodes are used in a selection code which is formed in a case of L=4. Specifically, if the selection code shown in Table 1 is used, a selection code for three lines which correspond to row electrodes 2-4 is used to apply selection pulses. It is not always necessary to select the three rows corresponding to the row electrodes 2-4, but a group of row electrodes 1-3 may be selected to apply the selection pulses.

The application of voltages to the column electrodes is determined as follows. Namely, with respect to a display information, the vectors $D_i$ for the display information are prepared by adding an imaginary display information. On the other hand, with respect to the selection pattern, there is used a selection pattern for the selection code applied to an L number of row electrodes which has been used to form the selection code for an $L_r$ number of row electrodes. Then, in the same manner as described before, exclusive OR operations are conducted to corresponding elements of the display information and the selection pattern to thereby obtain the sum i, whereby voltages to be applied to column electrodes are determined.

The above-description concerns the case that the L number of row electrodes which constitute a row electrode subgroup are real electrodes. However, it is possible to treat a part of the row electrodes as imaginary electrodes.

In this case, the number of selection pulses necessary for selection and the number of voltage levels to be applied to row electrodes become larger than minimum values with respect to the row electrodes which constitute real row electrode subgroups. However, this is sometimes advantageous when the voltage level to be applied to the column electrodes are used as voltage levels applied to other devices.

The driving method of the present invention is suitably applied to a twisted nematic liquid crystal display element, in particular to a so-called super-twisted nematic liquid crystal display element to which multiplied driving is applicable. The super-twisted nematic liquid crystal display element is so adapted to increase the twist angle of the liquid crystal molecules between both electrodes to cause a sharp change in the voltage-transmittance characteristic to thereby obtain a high density dot matrix display. (T. J. Scheffer and J. Nehring, Appl., Phys., Lett. 45(10) 1021-1023 (1984))

The method proposed in the article has drawbacks as follows. Since the product value $\Delta n \cdot d$ of the birefrigent index $\Delta n$ of the liquid crystal and the thickness d of the liquid crystal layer of a liquid crystal display element is substantially in a range of 0.8 μm-1.2 μm (Japanese Unexamined Patent Publication No. 10720/1985), a display having a good contrast ratio can not be obtained unless a specified combination of hue such as yellowish green and dark blue, bluish purple and pale yellow, and so on is used, and accordingly, it is impossible to provide a monochrome display. Further, it is impossible to obtain a multi-color or a full-color display by combining a multi-color filter.

In order to eliminate the above-mentioned problem, there is a proposal to obtain a liquid crystal display element capable of providing a monochrome display and having a high contrast ratio in which two layers of liquid crystal cells which have spiral structures opposite to each other are laminated and in which a voltage is applied to only one cell and the other cell is used merely as an optically compensating plate (Technology report of Television Association by Okumura et al, 11(27), p. 79, (1987)).

As another method, there is proposed a liquid crystal display element which comprises a liquid crystal layer including a nematic liquid crystal containing chiral material and a positive dielectric anisotropy and whose twisting angle is in a range of 160°-300°, the liquid crystal layer being interposed between a pair of substrates with transparent electrodes each having an orientation control film which are disposed in substantially parallel, and a driving means to apply a voltage across the transparent electrodes of the upper and lower substrates which hold the liquid crystal layer therebetween, wherein at least one birefrigent plate and a pair of polarization plates are disposed at an outside of the liquid crystal layer.

According to this method, a light, compact monochrome display type liquid crystal element can be obtained. The driving method of the present invention is suitable for such liquid crystal display element.

Preferred examples of the present invention will be described.

Figure 6:
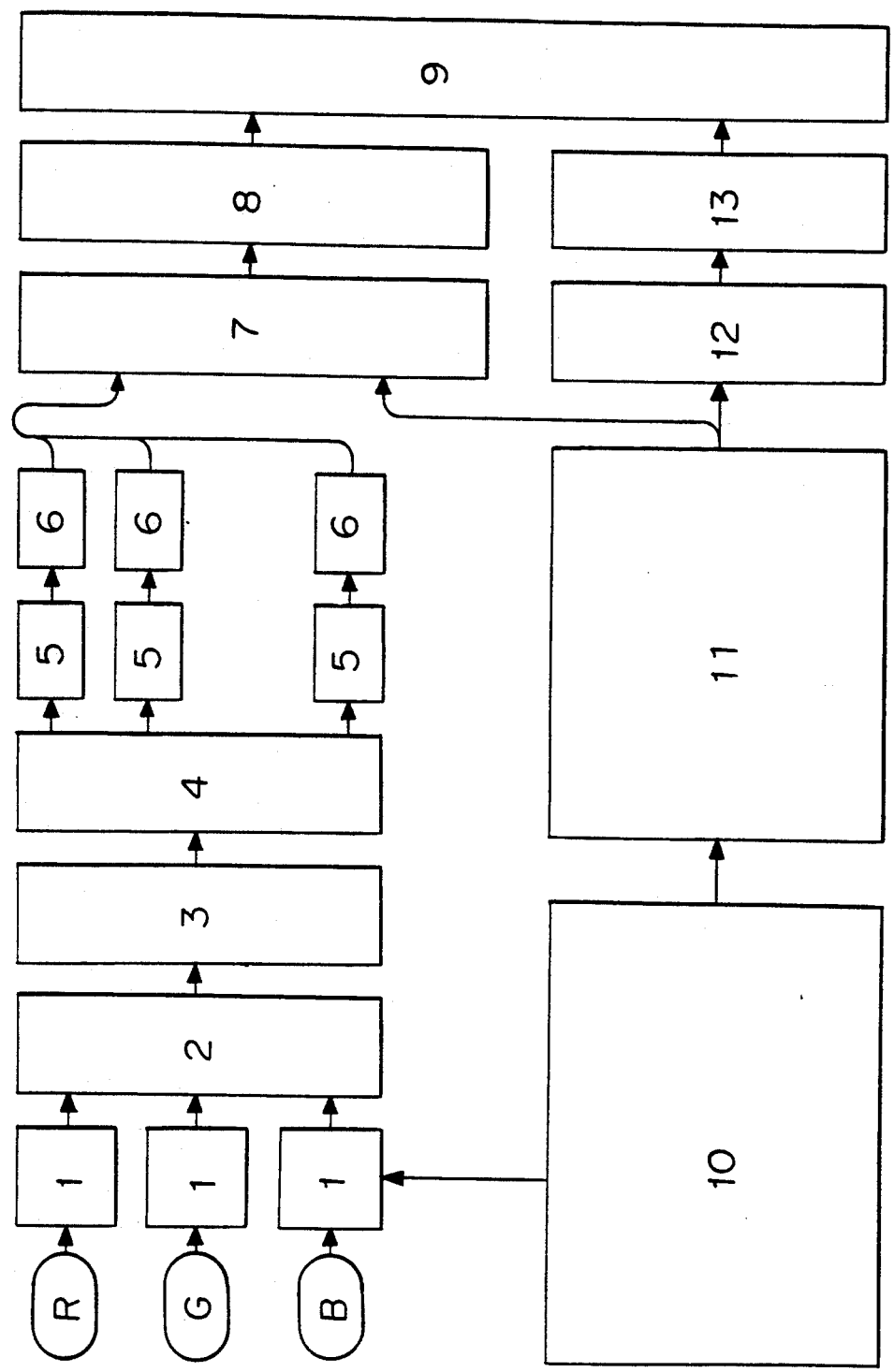
FIG. 6 is a block diagram showing an example of a circuit for realizing the driving method of the present invention.

FIG. 6 is an example of a circuit used to realize the driving method of the present invention. The circuit is adapted to display 16 degrees of gradation. As display data, analogue signals are inputted for R, G, B colors separately. The signals are respectively inputted to 6-bit A/D transducers 1, 1, 1 for R, G and B to be converted into digital data. The converted digital data signals are corrected (so-called $\gamma$ correction) at a corrector 2 so as to meet the optical characteristic of liquid crystal and are transformed into data indicating gradation having a predetermined bit number which is determined by a degree of gradation, the data being received in a display memory 3. Then, the data are read from the display memory 3 in a predetermined order, and are introduced into a data selector 4 where the data are assigned to an L number of subgroup memories, 5, 5, . . . , 5. The L number of data are inputted to gradation controlling circuits 6, 6, . . . , 6 where 15 cycles are collected together to form data of 1-bit - ON-OFF display data rows (L number), and the data are supplied to an exclusive OR/adder 7 where the exclusive OR of the L bit data and the L bit line electrode selection pattern which is supplied from a line electrode selection pattern generating circuit 11 are obtainable, and subsequently an adding operation is conducted. The data from the adder 7 are supplied to a column electrode driver 8. The line selection pattern is delayed for a time corresponding to the selection of one line at a delay circuit 12 and is supplied to a line electrode driver 13. Each output from the line electrode driver 13 and the column electrode driver 8 is inputted to each electrodes of a liquid crystal panel 9. Reference numeral 10 designates a timing generating circuit.

Figure 13:
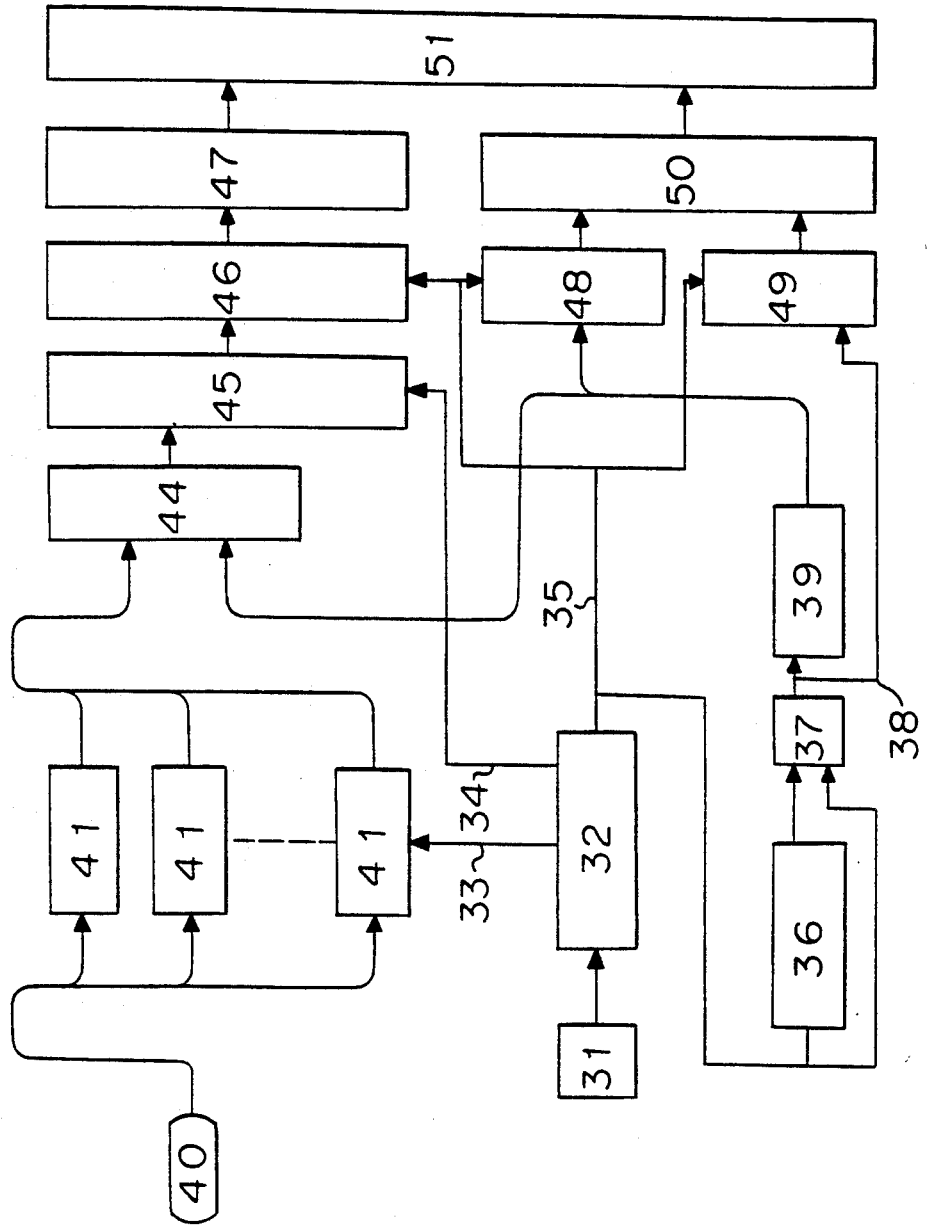
FIG. 13 is a block diagram showing an example of a circuit for realizing the driving method of the present invention.

FIG. 13 is a diagram showing a circuit wherein a selection code including all possible states of electric potential is used.

Assuming that a liquid crystal display element having an $N_1$ number of row electrodes and an $N_2$ number of column electrodes is used, and the $N_1$ number of line electrodes are divided into subgroups each having an L number of row electrodes in order to select each of the subgroups as a batch. A display information is displayed by transferring $\alpha$ bit parallel data.

The formation of selection signals are conducted as follows.

First of all, a clock signal is generated from a pulse generator 31. The pulse train is inputted to a clock terminal of an address counter 32 to form a clock signal 34. The clock signal 34 is inputted to a clock terminal of an $N_2$ stage shift register 45. The pulse signal is also divided in the address counter 32 to generate a load signal 35. The load signal is supplied to a clock terminal of a subgroup counter 36, a clock terminal of a flip-flop 37, a load terminal of an $N_2$ stage data latch 46, clock terminals of an L bit latch 48 and a clock terminal of $N_1/L$ stage shift register 49.

Further, the load signal 35 is divided in the subgroup counter 36 to be formed into an $L/N_1$ signal which is inputted to a data terminal of the flip-flop 37. The output of the flip-flop 37 is respectively inputted to a clock terminal of a row stage counter 39 and a data terminal of the signal $N_1/L$ stage shift resistor 49. The output of an L bit signal from the row stage counter 39 is inputted to each data terminal of the L bit data latch 48 directly or after the signal has been transformed into a gray code or any other code as necessary.

The outputs of the L bit data latch 48 and the output of the $N_1/L$ stage shift register 49 are inputted to an $N_1$-bit-3-level driver 50 from which an $N_1$ number of outputs are generated and they are inputted to row electrodes of a liquid crystal panel 51.

ON and OFF signals corresponding to the data of a display information are prepared as follows. Data 40 are sequentially written as $\alpha$-bit data in L number of RAMs 41, 41, . . . , 41 for rows of $Lk+1, Lk+2, \ldots, Lk+L$ ($k=0, \ldots, N_1/L-1$). On the other hand, the output of address counter 32 is inputted as an RAM address signal 33 to each of the L number of the RAMs 41, 41, . . . , 41 in FIG. 13.

The data of the display information are simultaneously read from the L number of the RAMs 41, 41, . . . , 41. An exclusive OR operation is conducted on the read-out data and the value of the corresponding row select pattern of the row stage counter 39, followed by summing a resulted value at an exclusive OR/adder 44 to thereby obtain g-bit data. The resulted g-bit data are inputted to the data terminal of the $N_2$ stage shift register 45 in which the data are sequentially shifted in accordance with the clock signal 34 to form complete $N_2$ stage data. When the complete data are formed, they are supplied to the $N_2$ stage latch 46 and are memorized when the load signal 35 is inputted. The output of the $N_2$ stage latch 46 is inputted to an $N_2$ number of L+1 level drivers 47. An $N_2$ number of outputs of the L+1 level drivers 47 are respectively inputted to column electrodes of the liquid crystal panel 51.

EXAMPLE 1

Figure 14:
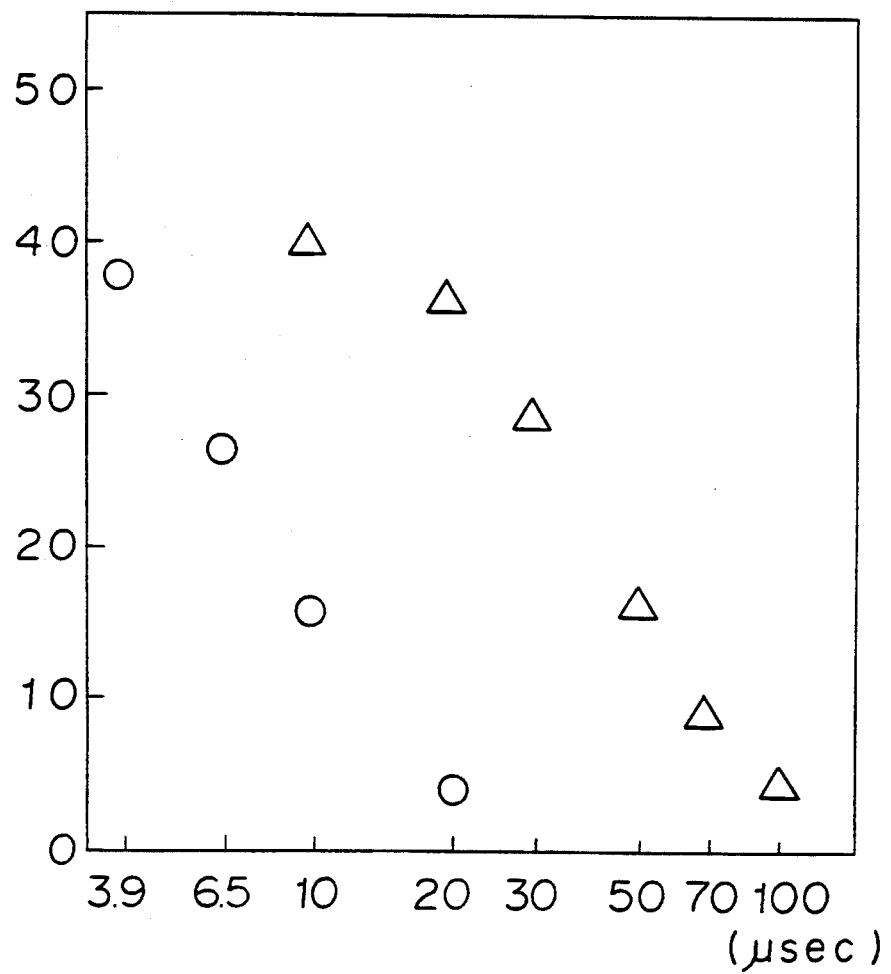
FIG. 14 is a graph showing changes of the contrast ratios according to a conventional method and the present invention wherein the width of a selection pulse is changed.

A STN liquid crystal display element having an average response speed of 50 msec (25° C.) was prepared by using the circuit structure as above-mentioned in which the number of the line electrodes was 490 and a selection of L=7, J=70 and K=8 was made. The liquid crystal display element was driven in accordance with the driving method of the present invention wherein the width of selection pulses for a selection pattern was changed. As a result, the highest contract ratios were obtained at 25° C. as shown by triangular marks in FIG. 14.

The liquid crystal used contained 30 wt % of difluorostilbene type liquid crystal and 43 wt % of tolan type liquid crystal, and as the characteristics of the liquid crystal as a whole, it shows 0.237 of refractive index anisotropy $\Delta n$, 12.1 cSt of viscosity $\eta$ and 86.7° C. of transparent point $T_c$. The thickness d of the liquid crystal layer was 3.7 $\mu$m.

In driving the liquid crystal display element, the selection code shown in Table 13 was used, which was a modification of a selection code formed from an 8×8 Hadamard's matrix as shown in Table 14 and which was a selection code corresponding to row electrodes 2-row electrodes 8. Further, in driving, whenever a selection pattern was applied to a row electrode, the next row electrode subgroup was applied, and $V_i = -V_0(L-2i)/L$ and $V_r = V_0 N^{\frac{1}{2}}/L$ were selected, whereby adjustment was made so as to obtain the highest contrast ratio in the absolute value of voltage. In Examples described below, whenever a selection pattern was applied to a row electrode, the next row electrode subgroup was applied.

TABLE 13

|       | 1 | 2 | 3 | 4 | 5 | 6 | 7 | 8 | 9 | 10 | 11 | 12 | 13 | 14 | 15 | 16 |
|-------|---|---|---|---|---|---|---|---|---|----|----|----|----|----|----|----|
| Row 1 | 1 | 0 | 1 | 0 | 1 | 0 | 1 | 0 | 0 | 1  | 0  | 1  | 0  | 1  | 0  | 1  |
| Row 2 | 1 | 1 | 0 | 0 | 1 | 1 | 0 | 0 | 0 | 0  | 1  | 1  | 0  | 0  | 1  | 1  |
| Row 3 | 1 | 0 | 0 | 1 | 1 | 0 | 0 | 1 | 0 | 1  | 1  | 0  | 0  | 1  | 1  | 0  |
| Row 4 | 1 | 1 | 1 | 1 | 0 | 0 | 0 | 0 | 0 | 0  | 0  | 0  | 1  | 1  | 1  | 1  |
| Row 5 | 1 | 0 | 1 | 0 | 0 | 1 | 0 | 1 | 0 | 1  | 0  | 1  | 1  | 0  | 1  | 0  |
| Row 6 | 1 | 1 | 0 | 0 | 0 | 0 | 1 | 1 | 0 | 0  | 1  | 1  | 1  | 1  | 0  | 0  |
| Row 7 | 1 | 0 | 0 | 1 | 0 | 1 | 1 | 0 | 0 | 1  | 1  | 0  | 1  | 0  | 0  | 1  |

TABLE 14

|       | 1 | 2 | 3 | 4 | 5 | 6 | 7 | 8 | 9 | 10 | 11 | 12 | 13 | 14 | 15 | 16 |
|-------|---|---|---|---|---|---|---|---|---|----|----|----|----|----|----|----|
| Row 1 | 1 | 1 | 1 | 1 | 1 | 1 | 1 | 1 | 0 | 0  | 0  | 0  | 0  | 0  | 0  | 0  |
| Row 2 | 1 | 0 | 1 | 0 | 1 | 0 | 1 | 0 | 0 | 1  | 0  | 1  | 0  | 1  | 0  | 1  |
| Row 3 | 1 | 1 | 0 | 0 | 1 | 1 | 0 | 0 | 0 | 0  | 1  | 1  | 0  | 0  | 1  | 1  |
| Row 4 | 1 | 0 | 0 | 1 | 1 | 0 | 0 | 1 | 0 | 1  | 1  | 0  | 0  | 1  | 1  | 0  |
| Row 5 | 1 | 1 | 1 | 1 | 0 | 0 | 0 | 0 | 0 | 0  | 0  | 0  | 1  | 1  | 1  | 1  |
| Row 6 | 1 | 0 | 1 | 0 | 0 | 1 | 0 | 1 | 0 | 1  | 0  | 1  | 1  | 0  | 1  | 0  |
| Row 7 | 1 | 1 | 0 | 0 | 0 | 0 | 1 | 1 | 0 | 0  | 1  | 1  | 1  | 1  | 0  | 0  |
| Row 8 | 1 | 0 | 0 | 1 | 0 | 1 | 1 | 0 | 0 | 1  | 1  | 0  | 1  | 0  | 0  | 1  |

COMPARATIVE EXAMPLE 1

The liquid crystal display element having the same structure as Example 1 was driven by using the conventional optimized amplitude selective addressing method at 1/480 duty and 1/15 bias wherein the width of selection pulses was changed. As a result, the highest contrast ratios were obtained as shown by circle marks in FIG. 14. From FIG. 14, it is understood that there is a great difference in contrast ratio at or near a pulse width of 20 μsec (a frame frequency of about 100 Hz), which is generally used in the optimized amplitude selective addressing method at 1/480 duty, between the present invention and the conventional method. Thus, it is understood that the relaxation phenomenon of the liquid crystal is suppressed and the contrast ratio is extremely high in the present invention.

EXAMPLE 2

A STN liquid crystal display element having an average response speed of 250 msec (25° C.) was prepared by using the circuit structure as above-mentioned in which the number of the line electrodes was 490 and a selection of L=7, J=70 and K=8 was made.

Figure 15:
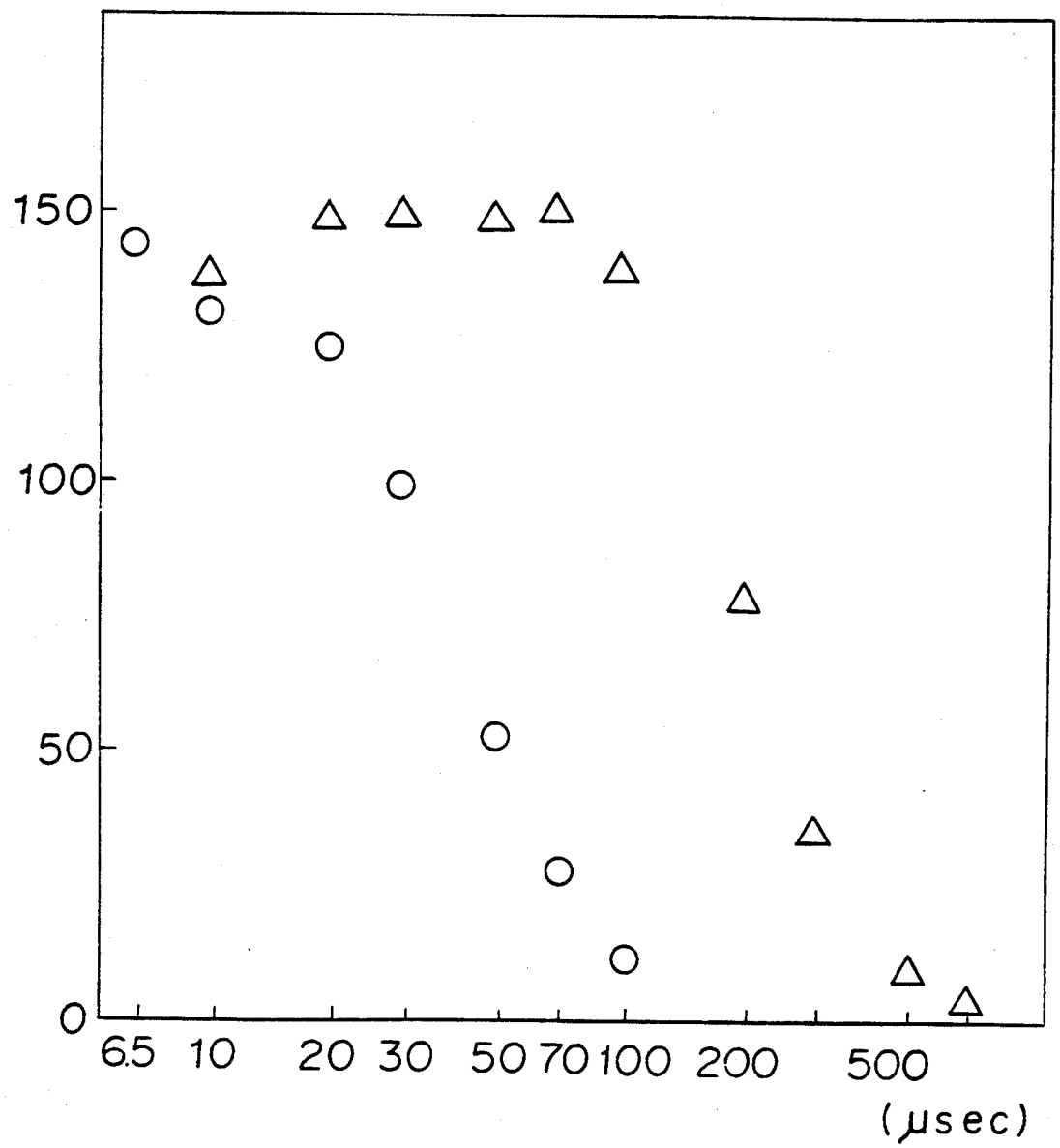
FIG. 15 is an another graph showing changes of the contrast ratios in accordance with conventional method and the present invention wherein the width of a selection pulse is changed.

The liquid crystal display element was driven in accordance with the driving method of the present invention wherein the width of selection pulses for a selection pattern was changed. As a result, the highest contract ratios were obtained at 25° C. as shown by triangular marks in FIG. 15.

The liquid crystal used does not contain either difluorostilbene type liquid crystal or a tolan type liquid crystal, and as the characteristics of the liquid crystal as a whole, it shows 0.131 of refractive index anisotropy Δn, 18.9 cSt of viscosity η, and 93.9° C. of $T_c$. The thickness d of the liquid crystal layer was 6.7 μm.

In this case, a selection code used was the same as that used in Example 1. Further, whenever one of the selection patterns was applied to a line electrode, the next line electrode subgroup was applied, and $V_i = -V_0(L-2i)/L$ and $V_r = V_0 N^{\frac{1}{2}}/L$ were selected, whereby adjustment was made so as to obtain the highest contrast ratio in the absolute value of voltage.

COMPARATIVE EXAMPLE 2

The liquid crystal display element having the same structure as Example 2 was driven by using the conventional optimized amplitude selective addressing method at 1/480 duty and 1/15 bias wherein the width of selection pulses was changed. As a result, the highest contrast ratios were obtained as shown by circle marks in FIG. 15. From FIG. 15, it is found that there is an influence by relaxation of the liquid crystal at or near a pulse width of 20 μsec (a frame frequency of about 100 Hz), which is generally used in the voltage averaging method (1/480 duty), and the contrast ratio decreases in comparison with the driving method of the present invention. However, the pulse width can be much longer than the conventional method for the same contrast ratio.

EXAMPLE 3

A STN liquid crystal display element having an average response speed of 80 msec (25° C.) was prepared in which the number of the line electrodes was 240 and a selection of L=7, J=34, K=8 and $L_r$=5 was made. The liquid crystal display element was driven in accordance with the driving method of the present invention wherein the width of selection pulses for a selection pattern was 20 μsec, and the selection code of Table 13 was used. As a result, the highest contract ratio was 80:1 at 25° C.

The liquid crystal used did not contain a difluorostilbene type liquid crystal, but contains 61 wt % of a tolan type liquid crystal, and as the characteristics of the liquid crystal as a whole it shows 0.229 of refractive index anisotropy Δn, 17.4 cSt of viscosity η and 89.2° C. of $T_c$. The thickness d of the liquid crystal layer was 3.9 μm.

EXAMPLE 4

The same STN liquid crystal display element as in Example 3 was used wherein although L=7, one of the electrodes was a dummy electrode and the number of actually used electrodes was 6 in a line electrode subgroup. The liquid crystal display element has 40 subgroups (J=40). The display element was driven by using the driving method of the present invention under the condition that the width of selection pulses corresponding to a selection pattern was 20 μsec, and the same selection code as in Example 3 was used. As a result, the highest contrast ratio was 75:1 at 25° C. In this case, however, the display cycle was slightly long because the number of the row electrode subgroups was larger than that of Example 3.

COMPARATIVE EXAMPLE 3

The liquid crystal display element having the same structure as Example 3 was driven by using the conventional method at 1/240 duty, 1/15 bias and a selection pulse width of 20 μsec. As a result, the highest contrast ratio was 55:1.

EXAMPLE 5

A STN liquid crystal display element, which was different from that of Example 3, having an average response speed of 80 msec, (25° C.), N=240 and L=4 was prepared. The liquid crystal display element was driven with a selection pulse width of 20 μsec by using a selection code consisting of all possible 16 ($=2^4$) number of selection patterns shown in Table 5. As a result, the highest contrast ratio was 80:1 although a time necessary to complete a display cycle was twice as much as that of Example 3.

The liquid crystal didn't contain a difluorostilbene type liquid crystal, but contains 61 wt % of a tolan type liquid crystal, and as the characteristics of the liquid crystal as a whole, it showed 0.224 of refractive index anioscopy $\Delta n$, 22.2 cSt of viscosity $\eta$ and 89.4° C. of $T_c$. The thickness d of the liquid crystal layer was 3.9 μm.

EXAMPLE 6

A STN liquid crystal display element having the same structure as Example 5 except that N=240 and L=4 was prepared. The liquid crystal display element was driven with a pulse width of 12 μsec by using a selection code consisting of all possible 16 ($=2^4$) selection patterns (IHAT) shown in Table 5. As a result, the highest contrast ratio was 75:1 at 25° C.

EXAMPLE 7

A STN liquid crystal display element having the same structure as Example 5 except that N=240 and L=4 was prepared. The liquid crystal display element was driven at a frame frequency of 90 Hz (i.e. a selection pulse width of about 11.6 μsec) by using a selection code consisting of all possible 16 ($=2^4$) selection patterns (IHAT) shown in Table 5. As a result, the highest contrast ratio was 80:1 at 25° C.

COMPARATIVE EXAMPLE 4

The STN liquid crystal display element having the same structure as Example 5 was driven by using the conventional method at 1/240 duty, 1/15 bias and a selection pulse width of 12 μsec. As a result, the highest contrast ratio was 55:1.

COMPARATIVE EXAMPLE 5

The STN liquid crystal display element having the same structure as Example 5 was driven by using the conventional method at 1/240 duty, 1/15 bias and a frame frequency of 90 Hz (a selection pulse width of about 46 μsec). As a result, the highest contrast ratio was 47:1.

COMPARATIVE EXAMPLE 6

The STN liquid crystal display element having the same structure as Example 5 was driven by using the IHAT method under the conditions of N=240, L=4 and a frame frequency of 90 Hz (a pulse of about 11.6 μsec) in such a manner that selection patterns were continuously applied to a line electrode subgroup, and the same selection patterns were applied to the next line electrode so as not to disperse the selection pulses. As a result, the highest contrast ratio was 30:1.

EXAMPLE 8

A STN liquid crystal display element having an average response speed of 45 msec (25° C.) was prepared wherein the number of line electrodes N was 240, and a selection of L=7, J=34, K=8 and $L_r$=5 was made. The liquid crystal display element was driven in accordance with the driving method of the present invention wherein the width of selection pulses corresponding to a selection pattern was 20 μsec. As a result, the highest contract ratio was 54:1 at 25° C.

The liquid crystal used contained 44 wt % of a difluorostilbene type liquid crystal but didn't contain a tolan type liquid crystal. As the characteristics of the liquid crystal as a whole, it shows 0.185 of refractive index anisotropy $\Delta n$, 13.8 cSt of viscosity $\eta$ and 92.2° C. of $T_c$. The thickness d of the liquid crystal layer was 4.7 μm.

EXAMPLE 9

The liquid crystal display element having the same construction as Example 8 was driven in the same manner as Example 8 except that in the row electrode selection patterns shown in Table 12, two row electrode subgroups were selected to be applied with a selection pattern (Table 12), and thereafter, the selection pattern adjacent to the right side of the applied selection pattern was used.

As a result, the highest contrast ratio was 54:1 which was substantially the same as that of Example 8. However, there was obtained a driving method capable of reducing the brightness nonuniformity of display and providing good look.

EXAMPLE 10

In the driving method of Example 9, whenever a display cycle has finished, selection was made by shifting one by one the relation of correspondence between the row electrodes of the row electrode subgroups and the elements of the selection patterns. The highest contrast ratio was 54:1, which was substantially the same as Example 8. The brightness nonuniformity in the display was further smaller than that of Example 9, and a display having a good look was obtained.

COMPARATIVE EXAMPLE 7

The STN liquid crystal display element having the same structure as Example 8 was driven by using the conventional method at 1/240 duty, 1/15 bias and with a selection pulse width of 20 μsec. As a result, the highest contrast ratio was reduced to 11:1.

EXAMPLE 11

A STN liquid crystal display element, which was separate from that of Example 8, having an average response speed of 45 msec (25° C.) was prepared. The liquid crystal display element was driven by using, as line electrode selection code, the inversion code shown in Table 6 and by making a selection of N=240, L=3 and a selection pulse width of 23 μsec. As a result, the highest contrast ratio was 50:1.

The liquid crystal used contained 44 wt % of a difluorostilbene type liquid crystal and 31 wt % of a tolan type liquid crystal, and as the characteristics of the liquid crystal as a whole, it showed 0.187 of refractive index anisotropy Δn, 15.1 cSt of viscosity η and 84.9° C. of $T_c$. The thickness d of the liquid crystal layer was 4.7 μm.

EXAMPLE 12

A STN liquid crystal display element having the same structure as Example 11 except that N=240 and L=3 was prepared. The liquid crystal display element was driven by using the driving method of the present invention by determining a selection pulse width of 23 μsec and selecting a frequency equalizing code as a line electrode selection code. As a result, the highest contrast ratio was 25:1.

EXAMPLE 13

The STN liquid crystal display element having the same structure as Example 11 was driven in the same manner as the driving method of Example 11 except that the selection pulse width was 12 μsec. As a result, the highest contrast ratio was 62:1.

COMPARATIVE EXAMPLE 8

The STN liquid crystal display element having the same structure as Example 11 was driven by using the conventional method at 1/240 duty, 1/15 bias and a frame frequency of 90 Hz (corresponding to a pulse width of 23 μsec). As a result, the highest contrast ratio was 18:1.

EXAMPLE 14

The STN liquid crystal display element having the same structure as Example 8 was used and a 4 degree gradation display of R, G and B colors was conducted by shifting the selection patterns in the same manner as Example 10. As the selection patterns, [S, S, S, −S, −S, −S] where 1st-8th selection patterns are expressed by a matrix S, was used. As a result, according to this driving method, a display having a high contrast ratio and capable of reducing unevenness could be obtained.

EXAMPLE 15

In the same manner as Example 14, selection patterns of [S, −S, S, −S, S, −S] were used. With respect to the contrast ratio and the unevenness, substantially the same degrees as those of Example 14 could be obtained. However, slight flicker was observed.

In accordance with the present invention, selection pulses are dispersed and exist in plural numbers in a single frame, whereby it is possible to reduce a change of optical state in comparison with the conventional method for a simple matrix system wherein there is only one selection pulse in a single frame. Accordingly, the driving method of the present invention is effective when a liquid crystal display element having an average response time of 200 msec or lower at a dynamic driving time, preferably 100 msec or lower, most preferably 50 msec or lower, is driven.

Further, since the driving method of the present invention can basically utilize the features of the IHAT method, a voltage to be supplied can be reduced in comparison with the conventional method when L≧4. In this case, if the value L is increased, the voltage to be supplied is further reduced. However, when the value L is large, the number of voltage level (L+1) of a waveform to be applied to column electrodes is also increased to thereby make hardware complicated. Accordingly, at present, it is possible to determine the value L to be 3-32, more preferably 7-15.

Since driver ICs for driving a liquid crystal display element can produce a $2^n$ (n is an integer) number of voltage levels, a generally used driver IC can be used for driving the liquid crystal display element if the number of line electrodes for a batch selection is ($2^n-1$), and therefore, it is practically useful.

Further, in accordance with the present invention, since the number of selection pulses necessary to display a display information is substantially increased in comparison with the conventional method, the present invention is effective in a case of driving fast response display. Further, the present invention permits a gradation display or a colored display which have a high contrast ratio.

Similarly, the driving method of the present invention can provide uniformity in a display in comparison with the conventional method.

In the conventional method, there was a large variation in the frequency components of a voltage waveform for driving depending on a display pattern, which caused brightness nonuniformity display. However, in accordance with the present invention, since there is a little fluctuation in the frequency components in a display pattern, it can suppress an uneven display.

We claim:

1. A driving method of a matrix type liquid crystal display element comprising at least J×L number (J and L are respectively integers of 2 or more) of row electrodes and a plural number of column electrodes wherein, said J×L number of row electrodes are divided into a J number of row electrode subgroups each comprising an L number of row electrodes so that said subgroups are selected as each batch to be driven;

when voltages are applied to the row electrodes, either a voltage level of $+V_r$ or $-V_r$ (where $V_r>0$) is applied at a selection time, when a voltage at a non-selection time is 0 (zero);

voltages applied to the column electrodes are selected from an (L+1) number of voltage levels of $V_0, V_1, \ldots, V_L$ (where $V_0<V_1<\ldots<V_L$); and when a two-valued information of the j-th line electrode subgroup (j is an integer of any of 1 through J) in a specified column in the plural column electrodes is expressed by a column vector $D_j$ having an L number of elements (where the elements of the vector $D_j$ comprise 1 indicating ON and 0 indicating OFF), the following conditions are satisfied:

(1) said j-th row electrode subgroup is selected by applying sequentially voltages so that the elements of a selection voltage vector which constitute a selection voltage matrix, as defined in the following items (a) and (b), correspond to voltages applied to the row electrodes constituting the j-th row electrode subgroups:

(a) a matrix $A=[\alpha_1, \alpha_2, \ldots, \alpha_q, \ldots, \alpha_k]$ (where $\alpha_q$ is a column vector having an L number of elements) comprising L rows and K columns, which has an element of $+V_r$ or $-V_r$ and in which the product of a matrix and a transposed matrix of the same assumes a scalar multiple of the unit matrix is selected (where K is an integer having a relation of $L \leq 2^p = K$ and p is a natural number), and (b) as said selection voltage, matrix comprising selection voltage vectors which include at least each one of $\alpha_1, \alpha_2, \ldots, \alpha_k, -\alpha_1, -\alpha_2, \ldots, -\alpha_k$ and are arranged in a matrix are selected, and, (2) when said j-th row electrode subgroup is selected under the above-condition (1), the voltages applied to the column electrodes to indicate a display information by means of the vector $D_j$ are determined as in the following items (a) and (b);

(a) a vector $\beta$ is formed by the selection voltages applied to the j-th row electrode subgroup where $+V_r$ represents 1 and $-V_r$ represents 0, and (b) a voltage $V_i$ (i is an integer of any of 0 through L) given by the sum of exclusive OR of the elements corresponding to the vectors $\beta$ and $D_j$ is applied to the column electrodes.

2. The driving method according to claim 1, wherein the selection vectors which constitute a selection voltage matrix comprise substantially each one of $\alpha_1, \alpha_2, \ldots, \alpha_k, -\alpha_1, -\alpha_2, \ldots, \alpha_k$.

3. The driving method according to claim 1, wherein the selection vectors which constitute a selection voltage matrix are so selected as to include all possible selection vectors.

4. The driving method according to claim 1, wherein a display information of the j-th row electrode subgroup in a specified column of the plural column electrodes has a gradation of (U+1) stages (where U is a natural number of 2 or more) in place of the two-valued information;

the selection voltage vectors which constitute a selection voltage matrix comprise substantially each 2KU number of $\alpha_1, \alpha_2, \ldots, \alpha_k, -\alpha_1, -\alpha_2, \ldots, -\alpha_k$ in which the selection voltage vectors are arranged in a matrix, are selected, and the selected vectors having the each 2KU number are used to display a gradation display of (U+1) stages by giving a specified ratio to the total U number of ON and OFF signs.

5. The driving method according to claim 4, wherein when a vector matrix $[\alpha_1, \alpha_2, \ldots, \alpha_k]$ is represented as S, as a unit, a selection voltage matrix having an arrangement $[S, S, \ldots, S, -S, -S, \ldots, -S]$ is used.

6. The driving method according to claim 1, wherein each time the voltages corresponding to selection voltage vectors as elements of the selection voltage matrix are applied to a row electrode subgroup, the voltages are applied to the next row electrode subgroups.

7. The driving method according to claim 1, wherein a selection voltage matrix which selects a row electrode subgroup has selection vectors the order of arrangement of which is shifted with respect to another selection voltage matrix which selects another row electrode subgroups.

8. The driving method according to claim 1, wherein a matrix in which a row of the matrix A which is used for forming a selection voltage matrix to display a former display information is replaced, is again used as the matrix A for forming selection voltage matrix.

9. The driving method according to claim 1, wherein an $(L - L_r)$ number of dummy row electrodes are added to a row electrode subgroup comprising an $L_r$ number of row electrodes (where $L_r < L$).

10. The driving method according to claim 1, wherein a part of an L number of row electrodes which constitutes a row electrode subgroup is an imaginary electrode or electrodes.

11. The driving method according to claim 1, wherein 3 through 32 row electrodes are driven as a batch.

12. The driving method according to claim 1, wherein a $(2^n - 1)$ number of row electrodes are driven as a batch.

13. The driving method according to claim 1, wherein said liquid crystal display element comprises a liquid crystal layer of a nematic liquid crystal in which a chiral material is contained, the dielectric anisotropy is positive and the twist angle is 160°-300°, a pair of substrates with transparent electrodes and orientation controlling films, which are disposed substantially in parallel and hold the liquid crystal layer therebetween, and a driving means to apply a voltage across the transparent electrodes of the pair of substrates which hold the liquid crystal layer.

14. The driving method according to claim 1, wherein said liquid crystal display element comprises a difluorostilbene type or a tolan type liquid crystal material.

* * * * *